United States Patent
Ishida et al.

(10) Patent No.: US 9,345,503 B2
(45) Date of Patent: May 24, 2016

(54) MEDICAL MANIPULATOR

(71) Applicant: Karl Storz GmbH & Co. KG, Tuttlingen (DE)

(72) Inventors: Shinji Ishida, Shizuoka (JP); Hiroaki Sano, Shizuoka (JP); Tsuneyoshi Suzuki, Tochigi (JP); Junichi Fukuda, Tochigi (JP)

(73) Assignee: Karl Storz GmbH & Co. KG, Tuttlingen (DE)

( * ) Notice: Subject to any disclaimer, the term of this patent is extended or adjusted under 35 U.S.C. 154(b) by 37 days.

(21) Appl. No.: 14/212,324

(22) Filed: Mar. 14, 2014

(65) Prior Publication Data

US 2014/0277107 A1    Sep. 18, 2014

(30) Foreign Application Priority Data

Mar. 14, 2013  (JP) ................................. 2013-051773

(51) Int. Cl.
*A61B 17/00* (2006.01)
*A61B 17/29* (2006.01)
*A61B 19/00* (2006.01)

(52) U.S. Cl.
CPC ....... *A61B 17/29* (2013.01); *A61B 2017/00314* (2013.01); *A61B 2017/00398* (2013.01); *A61B 2017/2929* (2013.01); *A61B 2019/2234* (2013.01); *A61B 2019/2238* (2013.01)

(58) Field of Classification Search
CPC ........... A61B 17/29; A61B 2017/2927; A61B 2017/2926; A61B 2017/2929; A61B 2017/00314; A61B 2017/00398; A61B 2019/2234; A61B 2019/2238
USPC ...................... 606/205–209, 130, 1
See application file for complete search history.

(56) References Cited

U.S. PATENT DOCUMENTS

| | | | |
|---|---|---|---|
| 5,439,478 A | | 8/1995 | Palmer |
| 5,643,294 A | * | 7/1997 | Tovey .................... A61B 17/29 606/148 |
| 5,928,136 A | | 7/1999 | Barry |
| 6,902,560 B1 | | 6/2005 | Morley et al. |
| 2004/0225323 A1 | | 11/2004 | Nagase et al. |
| 2008/0147113 A1 | | 6/2008 | Nobis et al. |
| 2009/0088785 A1 | * | 4/2009 | Masuda ......... A61B 17/320092 606/169 |
| 2010/0105843 A1 | | 4/2010 | Knott et al. |
| 2010/0160929 A1 | | 6/2010 | Rogers et al. |
| 2010/0331857 A1 | | 12/2010 | Doyle et al. |

FOREIGN PATENT DOCUMENTS

JP    4391762 B2    12/2009

* cited by examiner

*Primary Examiner* — Katrina Stransky
(74) *Attorney, Agent, or Firm* — Whitmyer IP Group LLC

(57) ABSTRACT

A medical manipulator has a distal-end working unit including an end effector. The distal-end working unit has a rotor having a hollow tube rotatable in unison with the end effector and a rotational support tube having a posture variable with respect to the shaft. The rotor is rotatably supported by an inner circumferential surface of the rotational support tube. Engaging members that are disposed in side holes formed in the rotational support tube have inner ends inserted in an annular groove.

10 Claims, 12 Drawing Sheets

MEDICAL MANIPULATOR

FIELD OF THE INVENTION

The present invention relates to a medical manipulator for use in surgical operations, especially endoscopic surgical operations, and more particularly to a medical manipulator that includes an end effector in a distal-end working unit which can be rolled in an unlimited angular range.

BACKGROUND OF THE INVENTION

In endoscopic surgery, also known as laparoscopic surgery, the surgeon makes a plurality of incisions in the abdominal region or the like of the patient, places respective trocars or tubular instruments in the incisions, and inserts a laparoscope (camera) and a plurality of pairs of forceps through the trocars into the body cavity to access the target region. Grippers for gripping a biological tissue or the like, scissors, electrosurgical scalpel blades, or the like are mounted as end effectors on the distal end portions of the forceps.

After having inserted the laparoscope and the forceps into the body cavity, the surgeon performs a surgical operation on the target region with the forceps while watching an image of the target region in the body cavity that is captured by the laparoscope and displayed on a display monitor which is connected to the laparoscope. Since the laparoscopic surgery does not require a laparotomy, it is less burdensome on the patient and greatly reduces the number of days required for the patient to spend in the hospital before recovering from the operation or being released from the hospital. The laparoscopic surgery is expected to increase a range of surgical operations to which it is applicable.

Forceps that are to be inserted through trocars include general forceps having no articulated joints on distal end portions thereof. Efforts are being made to develop another type of forceps that is categorized as a so-called medical manipulator having articulated joints on its distal end which make it possible for an end effector thereon to roll and tilt (see Japanese Patent No. 4391762, for example). Such a medical manipulator allows the end effector to move with greater freedom in body cavities, lets the surgeon practice surgical techniques easily, and is applicable to a wider range of surgical operations.

SUMMARY OF THE INVENTION

It is desirable for medical manipulators to have an increased number of degrees of freedom and as wide a movable range as possible for a distal-end working unit including an end effector. For example, if the distal-end working unit can roll in an unlimited angular range, then the medical manipulator is expected to contribute to smoother surgical techniques such as a tie-knotting or ligating technique. However, a medical manipulator with a distal-end working unit movable with more degrees of freedom tends to be more complex in structure.

It is an object of the present invention to provide a medical manipulator which includes a distal-end working unit movable with more degrees of freedom, but is not highly complex in structure.

To achieve the above object, there is provided in accordance with the present invention a medical manipulator comprising a handle, a shaft extending from the handle, a distal-end working unit having an end effector, the distal-end working unit being operatively coupled to the shaft for being tilted with respect to the shaft and rolled, and operating means disposed between the handle and the distal-end working unit, the operating means having a portion extending into the distal-end working unit for acting on the end effector, wherein the distal-end working unit has a rotor rotatable about a roll axis in unison with the end effector, the rotor having a hollow tube, and a rotational support tube having a posture variable with respect to an axial direction of the shaft, the rotor being rotatably supported by an inner circumferential surface of the rotational support tube, the rotor has a circumferentially extending annular groove defined in an outer circumferential surface thereof, the rotational support tube has a side hole extending through a wall thereof between inside and outside surfaces thereof, with an engaging member disposed in the side hole, and the engaging member is fixed to the rotational support tube while an inner end of the engaging member is inserted in the circumferentially extending annular groove.

With the above arrangement, since the rotor is hollow, the operating means, e.g., a drive member for opening and closing or rotating the end effector, and a conductive cable for supplying an electric current to the end effector, can be placed substantially centrally in the distal-end working unit, making it possible to provide a structure for rolling the distal-end working unit in an unlimited angular range. Since the rotational support tube is disposed outside, not inside, of the rotor, the space in the rotor can be used as a space in which the operating means is disposed, and the distal-end working unit can be simplified in structure. According to the present invention, therefore, the medical manipulator has the distal-end working unit that has a large number of degrees of freedom without constitutive complexities.

Furthermore, the engaging member is inserted in the side hole formed in the rotational support tube and is inserted in the annular groove in the rotor within the rotational support tube. Accordingly, the engaging member engages in the annular groove in the axial direction. This engaging structure allows the rotor to rotate relatively to the rotational support tube while preventing the rotor from axially moving with respect to the rotational support tube.

An alternative structure to be described below may also be effective to place the rotor rotatably, but axially immovably, with respect to the rotational support tube. The rotational support tube comprises two separate segment members, and the rotor has a circumferentially extending annular ridge on an outer circumferential surface thereof whereas each of the segment members has a circumferentially extending arcuate groove defined in an inner circumferential surface thereof. To assemble the alternative structure, the annular ridge that engages in the arcuate grooves prevents the rotor from moving axially with respect to the rotational support tube. The engaging structure according to the present invention makes it easier to perform accuracy management and requires a smaller number of manufacturing man-hours than the alternative structure since the arcuate groove does not have to be formed. The rotational support tube has its tubular shape accuracy maintained appropriately as it is free from deformations due to internal stresses which would otherwise tend to occur if grooves are formed.

The engaging member may be in the form of a pin. The area of contact between the engaging member in the form of a pin and the annular groove is small to lower frictional resistance therebetween, thereby minimizing resistance to the rotation of the rotor with respect to the rotational support tube. Consequently, the rotor can rotate smoothly with respect to the rotational support tube while at the same time the rotor is prevented from moving axially with respect to the rotational support tube.

The engaging member may comprise a plurality of engaging members provided at a plurality of locations that are angularly spaced circumferentially around the rotational support tube. The engaging members are highly effective to prevent the rotor from moving axially with respect to the rotational support tube.

The engaging member and the rotational support tube may be welded to each other by a single joint. The rotational support tube thus welded is not liable to be thermally deformed by a welding process and keeps a high dimensional accuracy for its hollow cylindrical shape.

The engaging members can be in form of a screw having an outer thread screwed into a corresponding thread in the side hole. This facilitates a disassembling of rotor and rotational support tube.

The medical manipulator according to the present invention has the distal-end working unit that has a large number of degrees of freedom without constitutive complexities.

DETAILED DESCRIPTION OF THE INVENTION

Medical manipulators according to preferred embodiments of the present invention will be described in detail below with reference to the accompanying drawings.

First Embodiment

Figure 1:
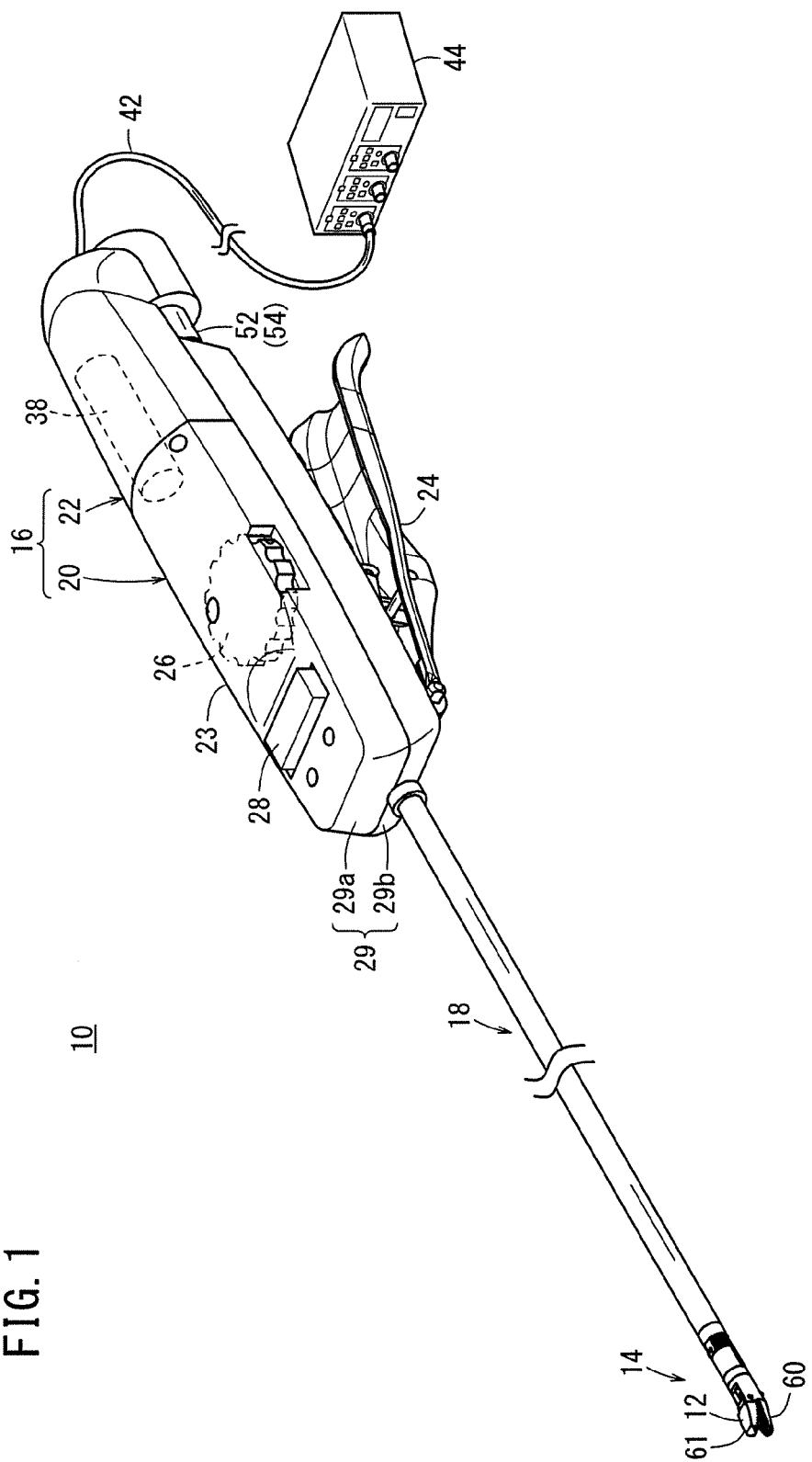
FIG. 1 is a perspective view, partly omitted from illustration, of a medical manipulator according to a first embodiment of the present invention.

FIG. 1 shows in perspective, partly omitted from illustration, a medical manipulator 10 according to a first embodiment of the present invention. As shown in FIG. 1, the medical manipulator 10 is a medical device having an end effector 12 on its distal end for gripping a needle, a suture, or a portion of a biological body or touching a biological body and treating the biological body. Depending on the type of the end effector 12, the medical manipulator 10 may be constituted as a needle driver, a pair of gripping forceps, a monopolar electrosurgical scalpel, a bipolar electrosurgical scalpel, or the like.

The general structure of the medical manipulator 10 which is constituted as a needle driver will first be described below, and then the constitutive details of the medical manipulator 10 will be described thereafter.

The medical manipulator 10 has a distal-end working unit 14 including the end effector 12, a handle 16 for actuating the end effector 12, and a shaft 18 interconnecting the end effector 12 and the handle 16. The end effector 12, which serves to perform surgical treatments, includes a pair of first and second gripper members 60, 61 as a gripper mechanism which can be opened and closed about an axis. The end effector 12 may alternatively be constituted as scissors or electrosurgical scalpel electrodes, rather than the gripper mechanism.

The distal-end working unit 14 including the end effector 12 can change its posture with respect to the shaft 18 with a plurality of degrees of freedom. According to the present embodiment, the distal-end working unit 14 can be "tilted" (swung) to the left and right from the longitudinal axis of the shaft 18 and can also be "rolled" about the longitudinal axis of the distal-end working unit 14. The distal-end working unit 14 may be tilted upwardly and downwardly, rather than being swung leftwardly and rightwardly, from the longitudinal axis of the shaft 18.

The shaft 18 is in the form of a long slender tubular member. The shaft 18 houses a plurality of members inserted and disposed in its space which make up a power transmitting mechanism for transmitting mechanical power required for opening and closing the end effector 12, and for tilting and rolling the distal-end working unit 14 from the handle 16 to the distal-end working unit 14.

The handle 16 has a handle body 20 housing a plurality of operating units therein and a drive unit 22 including a motor 38. The drive unit 22 is removably mounted on the handle body 20. When the motor 38 of the drive unit 22 mounted on the handle body 20 is energized, the drive power generated by the motor 38 is transmitted to the distal-end working unit 14. The handle body 20, the shaft 18, and the distal-end working unit 14 jointly make up a manipulator assembly. After the medical manipulator 10 has been used a predetermined number of times, the manipulator assembly may be removed from the drive unit 22 and discarded, and a new manipulator assembly may be connected to the drive unit 22. Therefore, the drive unit 22 is reusable in combination with a plurality of manipulator assemblies.

The handle body 20 includes a body section 23 connected to the proximal end of the shaft 18, a lever 24 (opening and closing member) pivotally mounted on the body section 23, a tilting wheel 26 (tilting member) housed in the body section 23, and a rolling switch 28 (rolling member) mounted on the body section 23.

The body section 23, which serves as a grip to be gripped by user when the user uses the medical manipulator 10, is shaped likes a stick extending longitudinally along the axial directions of the shaft 18. The body section 23 has a casing 29 that comprises an upper cover 29a and a lower cover 29b. The casing 29 houses therein various drive components including pulleys, gears, wires, etc.

The lever 24 which opens and closes the end effector 12 is pivotally mounted on a lower surface of the body section 23 so as to vertically swing about a distal end thereof. According to the present embodiment, the lever 24 is constituted as a manual operating member. When the user operates the lever 24, the manual operating force applied by the user is transmitted from the lever 24 to the end effector 12 of the distal-end working unit 14, opening or closing the end effector 12. Specifically, when the user opens the lever 24, i.e., when the user pushes the lever 24 away from the body section 23, the end effector 12 is opened, and when the user closes the lever 24, i.e., when the user pulls the lever 24 toward the body section 23, the end effector 12 is closed.

The tilting wheel 26 which tilts the distal-end working unit 14 is disposed substantially centrally in the longitudinal directions of the body section 23. The tilting wheel 26 is also constituted as a manual operating member, and has a circumferential edge protruding from the casing 29. When the user rotates the tilting wheel 26, the manual operating force applied by the user is mechanically transmitted through a tilting power transmitting system in the handle 16 and the shaft 18 to the distal-end working unit 14, tilting the distal-end working unit 14 into a direction not parallel to the axis of the shaft 18, i.e., into a leftward or right direction or an upward or downward direction.

The rolling switch 28 which rolls the distal-end working unit 14 is mounted on an upper surface of the body section 23 near its front end. According to the present embodiment, the rolling switch 28 is constituted as an electric operating member for applying an operation command to the motor 38 through a controller 44.

When the user presses the rolling switch 28, a signal depending on the position where the rolling switch 28 is pressed is electrically transmitted through a connector 54 and a cable 42 to the controller 44. Based on the transmitted signal, the controller 44 energizes the motor 38 to generate a rotary drive force, which is mechanically transmitted to the distal-end working unit 14, rotating the distal-end working unit 14 about the longitudinal axis thereof. According to the present embodiment, when the user presses a right region of the rolling switch 28, the distal-end working unit 14 rotates to the right, and when the user presses a left region of the rolling switch 28, the distal-end working unit 14 rotates to the left.

Figure 2:
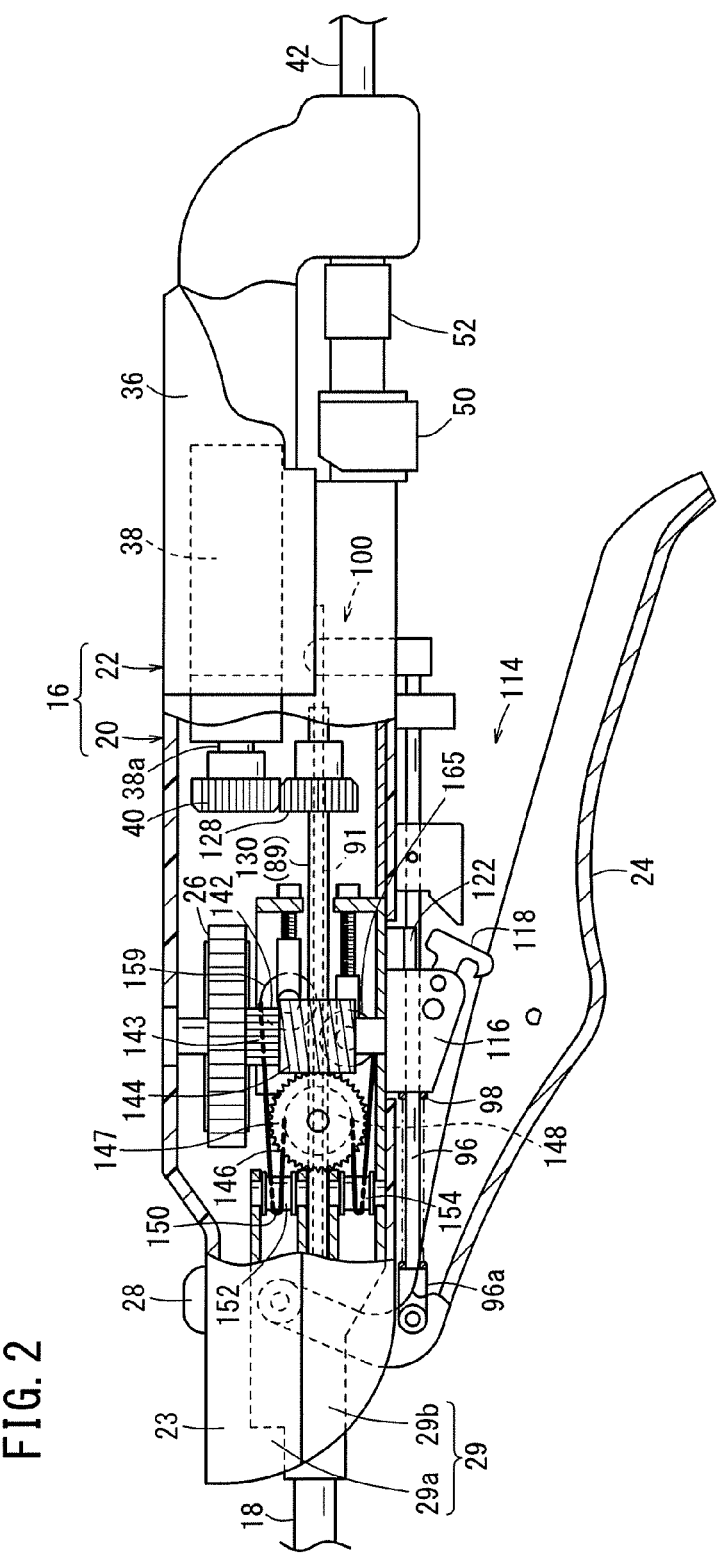
FIG. 2 is a fragmentary side view, partly in cross section, of a handle of the medical manipulator shown in FIG. 1.

As shown in FIG. 2, the drive unit 22 includes a housing 36, the motor 38 (drive source) which is disposed in the housing 36, and a drive gear 40 (pinion gear) fixed to an output shaft 38a of the motor 38. The drive unit 22 is removably mounted on a rear end of the handle body 20. When the drive unit 22 is mounted on, i.e., connected to, the handle body 20, the housing 36 and the handle body 20 jointly make up the casing 29 of the handle 16. According to the present embodiment, the housing 36 is of an elongate shape extending in the longitudinal directions of the handle body 20.

The drive unit 22 is electrically connected to the controller 44 by the cable 42 which includes a power line and a signal line. The controller 44 supplies electric power to the motor 38 and also supplies control signals for energizing the motor 38. The controller 44 receives electric power from an external power supply. When the user presses the rolling switch 28, the rolling switch 28 sends a signal to the controller 44, which controls the motor 38. The function of the controller 44 may be partly or wholly incorporated in the drive unit 22.

When the drive unit 22 is mounted on the body section 23 of the handle body 20, the drive gear 40 fixed to the output shaft 38a of the motor 38 is brought into mesh with a driven gear 128 disposed in the body section 23. When the motor 38 is then energized, the rotary drive force generated by the motor 38 is transmitted through the drive gear 40 and the driven gear 128 into the handle body 20.

As shown in FIG. 2, a handle connector 50 is mounted on the handle body 20, and a unit connector 52 is mounted on the drive unit 22. While the drive unit 22 is mounted on the handle body 20, the handle connector 50 and the unit connector 52 are electrically connected to each other. With the handle connector 50 and the unit connector 52 being connected, when the rolling switch 28 is pressed, the controller 44 energizes the motor 38 of the drive unit 22.

Figure 3:
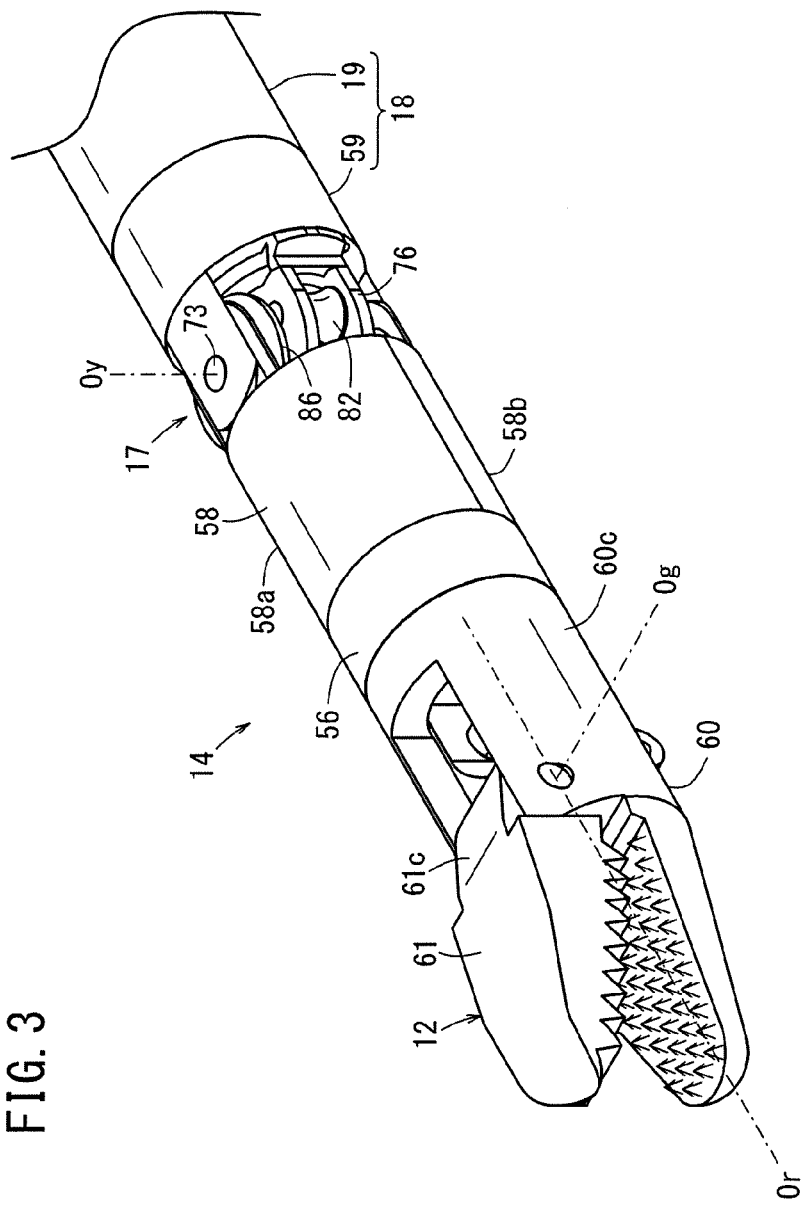
FIG. 3 is a perspective view of a distal-end working unit.
Figure 4:
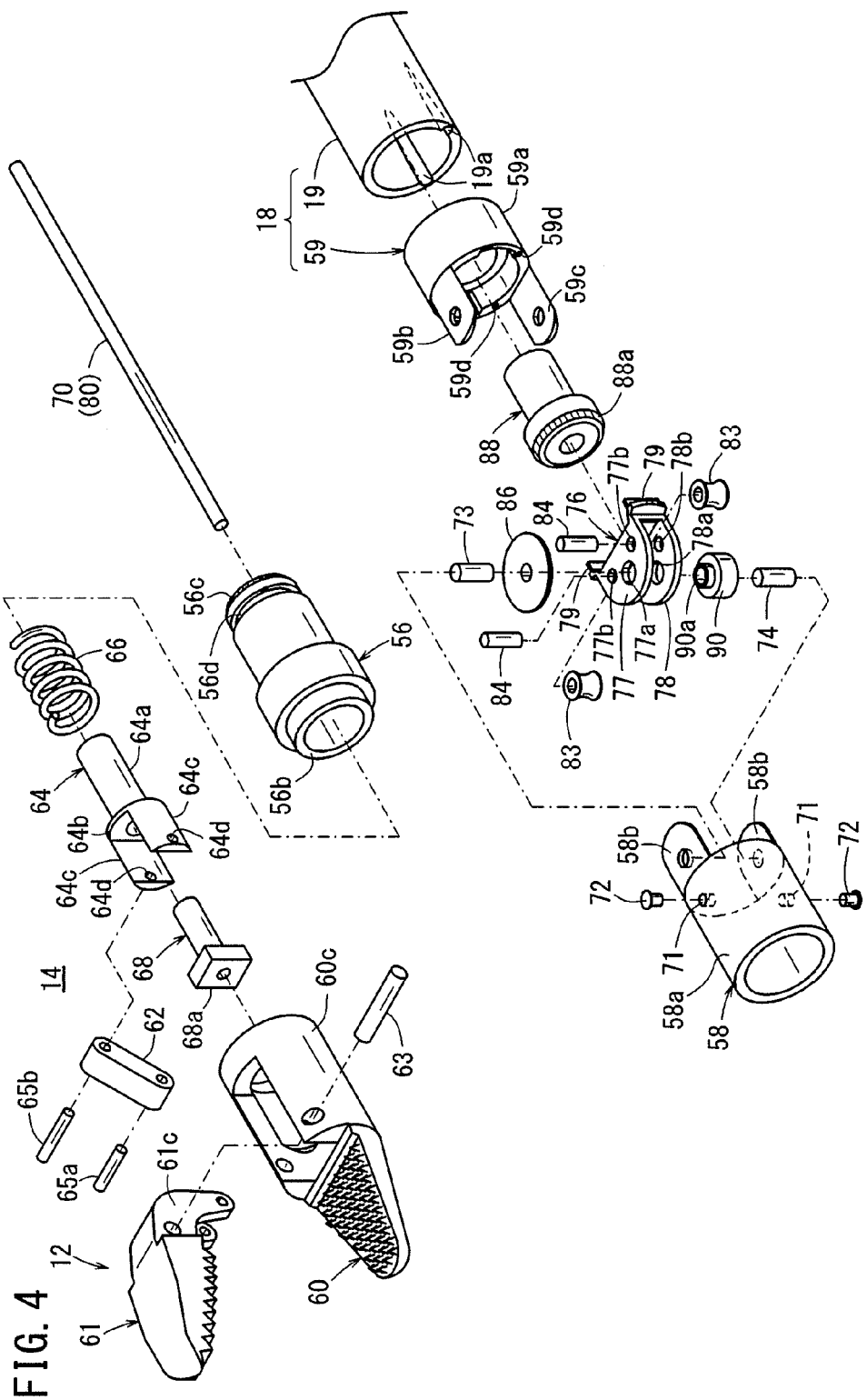
FIG. 4 is an exploded perspective view of the distal-end working unit.
Figure 5A:
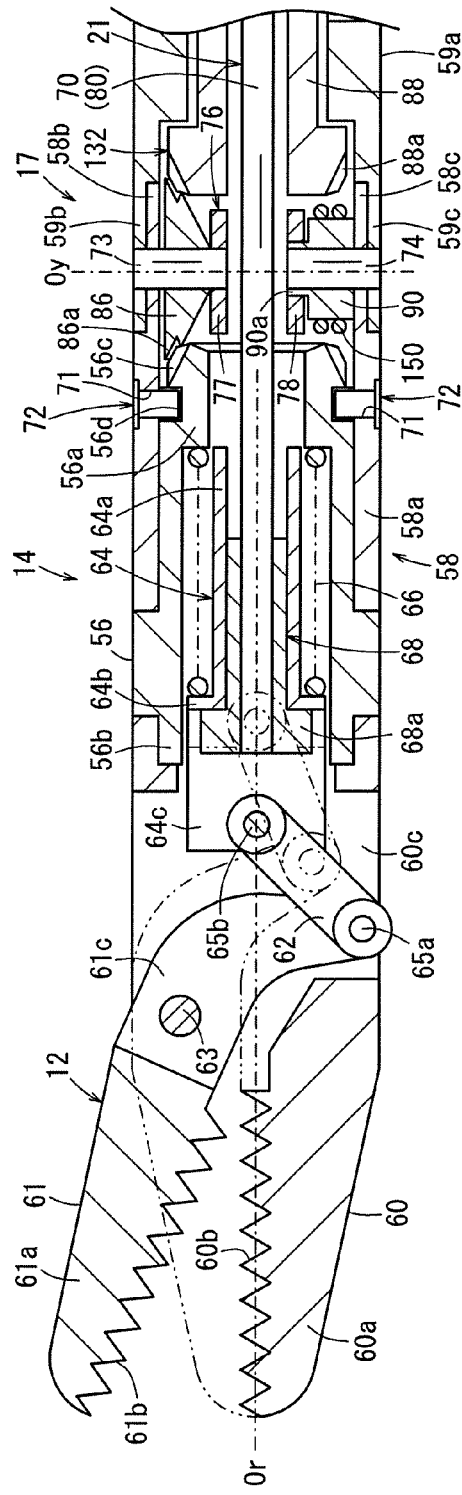
FIG. 5A is a vertical cross-sectional view of the distal-end working unit.

FIG. 3 shows in perspective the distal-end working unit 14 which is coupled to the front end of the shaft 18. FIG. 4 shows the distal-end working unit 14 in exploded perspective. FIG. 5A shows the distal-end working unit 14 in vertical cross section. As shown in FIGS. 3 to 5A, the distal-end working unit 14 includes the end effector 12 which can be opened and closed, a hollow tubular rotary sleeve 56 (rotor) to which the end effector 12 is fixed, and a rotational support tube 58 having an inner circumferential surface on which the rotary sleeve 56 is supported for rotation about its own axis.

The end effector 12 includes a first gripper member 60 and a second gripper member 61 which are rotatably coupled to each other by a pin 63, for turning about a gripper axis Og aligned with the pin 63. The first gripper member 60 has a proximal portion 60c, and the second gripper member 61 has a proximal portion 61c rotatably coupled to the proximal portion 60c by the pin 63. The first gripper member 60 has a gripping surface 60b and the second gripper member 61 has a gripping surface 61b. The gripping surface 60b of the first gripper member 60 and the gripping surface 61b of the second gripper member 61 serve to jointly grip an object to be gripped such as a needle or the like.

The proximal portion 61c of the second gripper member 61 is coupled to a transmitting member 64 by a link member 62. The proximal portion 61c and the link member 62, and the link member 62 and the transmitting member 64 are rotatably coupled to each other by respectively pins 65a, 65b. The transmitting member 64 has a guide tube 64a, a flange 64b disposed on a front end of the guide tube 64a, and a pair of parallel support arms 64c extending from edges of the flange 64b toward the distal end. The transmitting member 64 is axially movably disposed in the rotary sleeve 56. The pin 65b is fitted in pin holes 64d formed respectively in the support arms 64c.

A compression spring 66 is disposed between the transmitting member 64 and the rotary sleeve 56. The compression spring 66 has an end held against the flange 64b of the transmitting member 64 and another end held against a step 56a on the inner circumferential surface of the rotary sleeve 56. The compression spring 66 normally biases the transmitting member 64 to move resiliently toward the distal end.

An end collar 68 is inserted into the transmitting member 64 from the front end thereof. The end collar 68 has an engaging flange 68a on its distal end portion which engages the front end face of the guide tube 64a of the transmitting member 64. The end collar 68 is fixed to the front end of a pull wire 70 which extends through an articulated joint 17 (see FIGS. 5A and 6) between the distal-end working unit 14 and the shaft 18.

The pull wire 70 is a member that is movable back and forth in the shaft 18 and the distal-end working unit 14 in response to the user's action on the lever 24 of the handle 16. When the pull wire 70 is longitudinally displaced toward the proximal end, the end collar 68 that is secured to the pull wire 70 pushes the transmitting member 64 toward the proximal end. The transmitting member 64 is thus displaced toward the proximal end against the bias of the compression spring 66. As the transmitting member 64 is displaced toward the proximal end, it pulls the link member 62 to cause the second gripper member 61 coupled thereto to turn toward the first gripper member 60, so that the end effector 12 is closed. In FIG. 5A, the second gripper member 61 is indicated by the imaginary lines as being displaced to the first gripper member 60 until the gripping surface 61b of the second gripper member 61 and the gripping surface 60b of the first gripper member 60 contact each other.

When the pull wire 70 and the end collar 68 are displaced toward the distal end after the gripping surface 61b of the second gripper member 61 and the gripping surface 60b of the first gripper member 60 have contacted each other, the transmitting member 64 is also displaced toward the distal end under the bias of the compression spring 66. The transmitting member 64 pushes the link member 62 to cause the second gripper member 61 to turn away from the first gripper member 60, so that the end effector 12 is opened and returned to the original state. This shows that the opening and closing movements of the end effector 12.

In the present embodiment, the first gripper member 60 is constituted as a fixed gripper member and the second gripper member 61 as a movable gripper member, in the end effector 12. However, both the first gripper member 60 and the second gripper member 61 may be constituted as movable gripper members.

The rotary sleeve 56 has a reduced-diameter front end portion 56b securely fitted in the proximal portion 60c of the first gripper member 60. The rotary sleeve 56 also has a bevel gear 56c on its rear end and an annular groove 56d defined in an outer circumferential surface thereof and extending through 360° at a position closer to the front end thereof than the bevel gear 56c. The end effector 12, the rotary sleeve 56, the transmitting member 64, the end collar 68, and the compression spring 66 are rotatable in unison with respect to the rotational support tube 58 about a roll axis Or aligned with the longitudinal axis of the distal-end working unit 14.

The rotational support tube 58 has a tubular member 58a that has its posture variable around the axis of the shaft 18. The rotary sleeve 56 is rotatably supported by the inner circumferential surface of the tubular member 58a. The rotational support tube 58 has an outside diameter preferably in the range from 3 mm to 8 mm and an inside diameter preferably in the range from 2 mm to 7 mm.

Figure 5C:
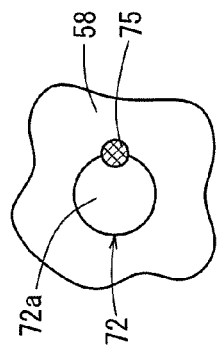
FIG. 5C is a view showing a joint between the engaging member and a rotational support tube.
Figure 5B:
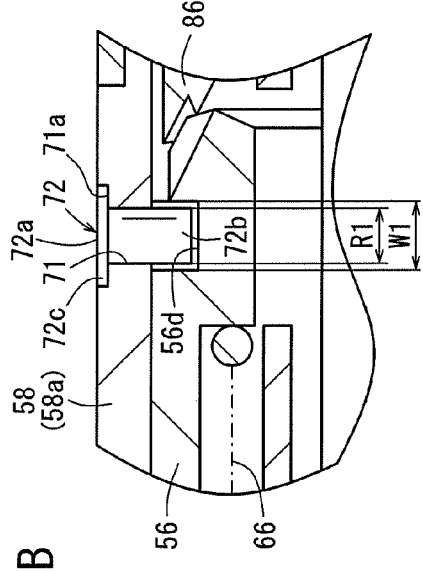
FIG. 5B is an enlarged vertical cross-sectional view of an engaging member and its peripheral parts of the distal-end working unit.

As shown in FIGS. 5A and 5B, the rotational support tube 58 has side holes 71 formed therein that extend through a wall thereof between inside and outside surfaces of the rotational support tube 58. In the illustrated embodiment, the side holes 71 are in the form of circular pin holes extending radially through the wall of the tubular member 58a of the rotational support tube 58. However, the side holes 71 may be in the form of oblong holes extending circumferentially through a predetermined angle. In the illustrated embodiment, the rotational support tube 58 has two side holes 71 disposed diametrically opposite to each other across the axis of the rotational support tube 58. However, the rotational support tube 58 may have a single side hole or three or more side holes angularly spaced at intervals in the circumferential directions.

Engaging members 72 are disposed in the respective side holes 71. Specifically, the engaging members 72 are inserted in the respective side holes 71 and fixed to the rotational support tube 58. In the illustrated embodiment, the engaging members 72 have outer ends 72a, i.e., ends near the rotational support tube 58, firmly secured to the rotational support tube 58 by an appropriate joining process such as welding, adhesive bonding, or the like, for example. The engaging members 72 have inner ends 72b, i.e., ends near the rotary sleeve 56, projecting inwardly from the inner circumferential surface of the rotational support tube 58 and inserted in the annular groove 56d defined in the rotary sleeve 56.

Each of the engaging members 72 is in the form of a pin. The outside diameter R1 of the inner end 72b is substantially the same as or slightly smaller than the width W1 of the annular groove 56d, i.e., the dimension of the angular groove 56d along the axis of the rotary sleeve 56. Each of the engaging members 72 is not limited to a pin shape, but may be of an arcuate shape extending in a predetermined angular range in the circumferential directions of the rotational support tube 58, for example.

As shown in FIG. 5B, the outer end 72a of each of the engaging members 72 has an annular flange 72c disposed in an annular large-diameter portion 71a in the outer end of one of the side holes 71. The engaging members 72 are thus accurately positioned with respect to the rotational support tube 58, and project from the inner circumferential surface of the rotational support tube 58 by a desired distance. If a small clearance is present between the inner end 72b of the engaging member 72 and the bottom of the annular groove 56d, as illustrated in FIG. 5B, then it effectively reduces the sliding resistance between the engaging member 72 and the annular groove 56d.

The engaging members can be in form of a screw having an outer thread screwed into a corresponding thread in the side hole. This facilitates a disassembling of rotor and rotational support tube.

The engaging members 72 fixed to the rotational support tube 58 engage in the annular groove 56d defined in the rotary sleeve 56. Therefore, the rotary sleeve 56 and the rotational support tube 58 are operatively coupled to each other such that the rotary sleeve 56 is rotatable, but axially immovable, with respect to the rotational support tube 58. The rotary sleeve 56 is thus prevented from being dislodged from the rotational support tube 58 by the engaging members 72 engaging in the annular groove 56d.

The distal-end working unit 14 is assembled by successively performing a process (inserting process) of inserting the proximal end of the rotary sleeve 56 into the rotational support tube 58 from its distal end, a process (engaging member placing process) of inserting the engaging members 72 into the respective side holes 71 formed in the rotational support tube 58 from outside of the rotational support tube 58 and placing the inner ends 72b of the engaging members 72 in the annular groove 56d of the rotational support tube 56, and a process (joining process) of jointing the rotational support tube 58 and the engaging members 72 by welding, adhesive bonding, or the like, for example. The rotary sleeve 56 is thus rotatably supported by the inner circumferential surface of the rotational support tube 58 while at the same time the rotary sleeve 56 is prevented from being dislodged from the rotational support tube 58.

If the rotational support tube 58 and the engaging members 72 are joined to each other by welding, then each of the engaging members 72 may be joined to the rotational support tube 58 by a single joint 75 (welded region), as shown in FIG. 5C in which the engaging member 72 is viewed from the outer end 72a. Since there is almost no load applied in a direction to pull the engaging member 72 from the side hole 71, the single joint 75 formed between each engaging member 72 and the rotational support tube 58 is enough to provide a sufficient joining strength. Therefore, even though the rotational support tube 58 and the engaging members 72 are joined to each other by welding, the rotational support tube 58 is not liable to be thermally deformed by the welding process and keeps a high dimensional accuracy for its hollow cylindrical shape.

The rotational support tube 58 is rotatably coupled to a fulcrum block 59 by joint pins 73, 74 for turning about a tilt axis Oy. The fulcrum block 59 is fixed to the distal end of a hollow shaft body 19 which serves as a body section of the shaft 18. The fulcrum block 59 and the shaft body 19 jointly make up the shaft 18.

In the present embodiment, the tilt axis Oy extends vertically. However, the tilt axis Oy may extend along any one of directions across the axis of the shaft body 19. The rotational support tube 58 has a pair of parallel tongue pieces 58b, 58c projecting toward the proximal end from respective upper and lower portions of the rear end of the tubular member 58a. The fulcrum block 59 has a tubular member 59a and a pair of parallel tongue pieces 59b, 59c projecting toward the distal end from respective upper and lower portions of the front end of the tubular member 59a. The joint pins 73, 74 are fitted in respective holes formed in the tongue pieces 58b, 58c of the rotational support tube 58 and the tongue pieces 59b, 59c of the fulcrum block 59.

Figure 6:
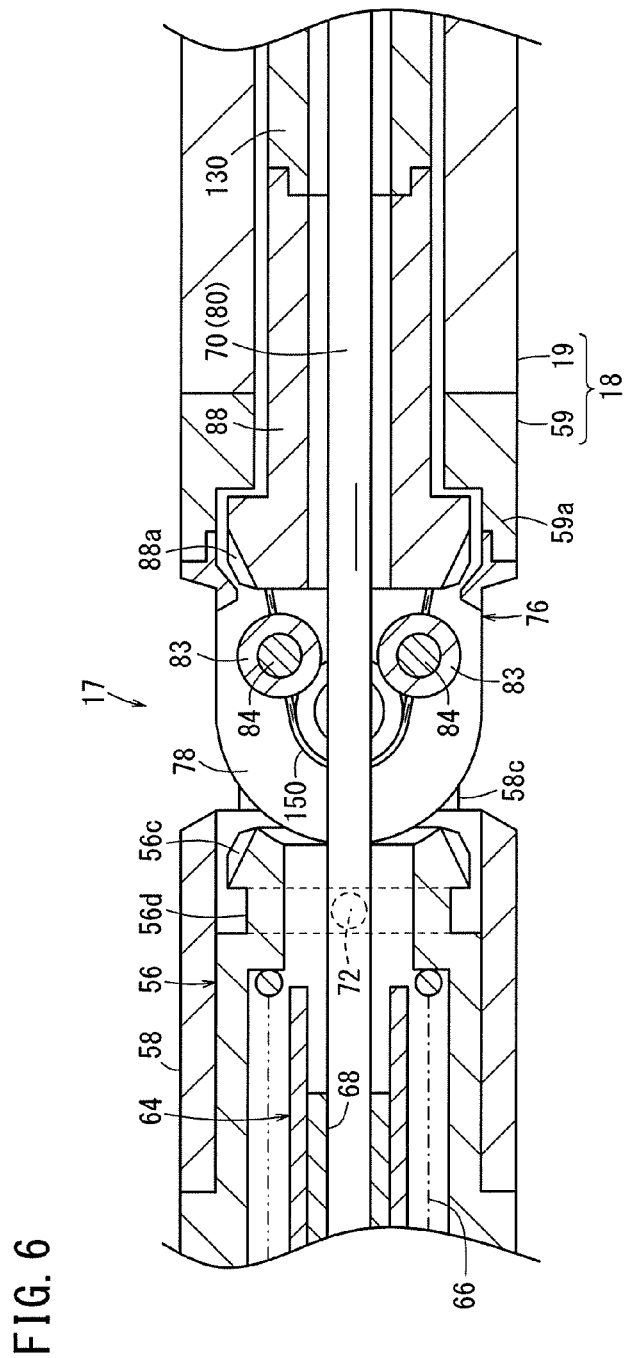
FIG. 6 is a vertical cross-sectional view of an articulated joint and its peripheral parts at the time the distal-end working unit is aligned straight with a shaft.

As shown in FIGS. 4, 5A, and 6, the articulated joint 17 includes a support block 76 that is mounted on the front end of the tubular member 59a of the fulcrum block 59. As shown in FIG. 4, the support block 76 has a pair of parallel upper and lower support plates 77, 78 which face each other and a pair of connectors 79 interconnecting left and right rear end portions of the support plates 77, 78. The upper support plate 77 has a pin hole 77a formed therein with the upper joint pin 73 inserted therein, and a pair of left and right pin holes 77b formed therein with upper ends of two pins 84 inserted respectively therein. The lower support plate 78 has a hole 78a formed therein with a reduced-diameter upper end 90a of a driven pulley 90 inserted therein, and a pair of left and right pin holes 78b formed therein with lower ends of the two pins 84 inserted respectively therein.

Guide rollers 83 for guiding the pull wire 70 are disposed respectively on left and right sides of the pull wire 70 of the distal-end working unit 14 near the tilt axis Oy about which the distal-end working unit 14 is tiltable with respect to the shaft 18. The guide rollers 83 are disposed rotatably supported on the respective two pins 84 that extend parallel to each other and are spaced from each other. The pull wire 70 extends through a gap between the two guide rollers 83.

As shown in FIG. 5A, the articulated joint 17 between the distal-end working unit 14 and the shaft 18 includes the pair of joint pins 73, 74 aligned with the tilt axis Oy. The pull wire 70, which serves as part of a gripper mechanism opening and closing drive force transmitter 80, is movable back and forth through the gap between the joint pins 73, 74 in directions perpendicular to the axes of the joint pins 73, 74.

A bevel gear 86 is rotatably supported by the upper joint pin 73 between the upper support plate 77 and the tongue piece 58b of the rotational support tube 58. The bevel gear 86 is rotatable independently of the upper support plate 77 and the tongue piece 58b. The bevel gear 86 has gear teeth 86a held in mesh with the bevel gear 56c on the rear end of the rotary sleeve 56 and a bevel gear 88a on the front end of a gear sleeve 88. The gear sleeve 88 having the bevel gear 88a is in the form of a hollow cylinder through which the pull wire 70 is inserted.

When the gear sleeve 88 is rotated about its own axis, a rotary drive force is transmitted from the gear sleeve 88 through the bevel gear 86 and the bevel gear 56c to the rotary sleeve 56. The rotary sleeve 56 and the end effector 12 coupled thereto are now rotated with respect to the rotational support tube 58 about the roll axis Or. This rotation is referred to as a rolling movement of the distal-end working unit 14.

The driven pulley 90 is rotatably supported by the lower joint pin 74 between the lower support plate 78 and the tongue piece 58c. The driven pulley 90 is fixed to an inner surface of the tongue piece 58c of the rotational support tube 58. The driven pulley 90 and the rotational support tube 58 including the tongue piece 58c are thus swingable together with respect to the fulcrum block 59. A tilting wire 150 is trained around the driven pulley 90. The tilting wire 150 has a portion fixed to the driven pulley 90 and extends through the shaft 18 into the handle 16. Details of a structure by which the tilting wire 150 is laid out will be described later.

When the driven pulley 90 is rotated about its own axis by the tilting wire 150, the rotational support tube 58 that is fixed to the driven pulley 90 is rotated in unison with the driven pulley 90. The distal-end working unit 14 which includes the rotational support tube 58, the rotary sleeve 56, and the end effector 12 is now turned with respect to the shaft 18 about the tilt axis Oy. This turning movement is referred to as a tilting movement of the distal-end working unit 14.

The distal-end working unit 14 can make a tilting movement in a range of certain areas on both a positive side (right side) and a negative side (left side) of a central position (reference position) at which the distal-end working unit 14 is aligned with the shaft 18. The tilting movement range of the distal-end working unit 14 is represented by +70° to −70°, for example.

The pull wire 70 has it proximal end portion coupled to the front end of a pull rod 91 (see FIG. 2). The pull wire 70 and the pull rod 91 are rotatable relatively to each other in a hollow shaft 89 (see FIG. 2) that is coupled to the proximal end of the gear sleeve 88. The pull wire 70 and the pull rod 91 are joined to each other such that a tensile force applied to the pull rod 91 in a direction toward its proximal end will be transmitted to the pull wire 70. When the pull rod 91 is displaced axially, the pull wire 70 that is joined to the pull rod 91 is also displaced axially, opening or closing the end effector 12. When the distal-end working unit 14 is rolled, the pull wire 70 rotates with respect to the pull rod 91. Therefore, the pull wire 70 does not present an obstacle to the rolling movement of the distal-end working unit 14.

As shown in FIG. 2, the pull rod 91 extends through the hollow shaft 89 and has its proximal end projecting from the proximal end of the hollow shaft 89. The lever 24 has a distal end portion swingably coupled to the body section 23 near the distal end portion thereof. A lever rod 96 has a distal end pivotally connected to the lever 24 near its distal end. The lever rod 96 is disposed beneath the body section 23 substantially parallel to a longitudinal axis of the body section 23, and is normally biased by a spring 98 move resiliently toward its distal end. A drive force applied from the lever 24 is transmitted to the lever rod 96 and then through an intermediate transmitting mechanism 100 to the pull rod 91 and the pull wire 70 (see FIG. 5A) for thereby opening or closing the end effector 12.

A mechanism for enabling the distal-end working unit 14 to make a rolling movement will be described below mainly with reference to FIGS. 2 and 5A. According to the present embodiment, the distal-end working unit 14 makes a rolling movement when the drive force from the motor 38 is transmitted to the distal-end working unit 14. A rolling drive mechanism for rolling the distal-end working unit 14 includes the motor 38, the drive gear 40 fixed to the motor 38, the driven gear 128 held in mesh with the drive gear 40, a rolling motion transmitting tube 130 to which the driven gear 128 is fixed, the bevel gear 86 held in mesh with the front end of the rolling motion transmitting tube 130, and the rotary sleeve 56 which is held in mesh with the bevel gear 86. The gear sleeve 88 and the hollow shaft 89 jointly make up the rolling motion transmitting tube 130. The rolling motion transmitting tube 130, the bevel gear 86, and the rotary sleeve 56 jointly make up a rotary motion transmitter 132 for transmitting a rotary drive force from the handle 16 to the distal-end working unit 14.

With the drive unit 22 mounted on the handle body 20 and the controller 44 electrically connected to the power supply, when the user who is gripping the handle 16 presses the rolling switch 28 shown in FIG. 1, the motor 38 is energized, generating a rotary drive force that is transmitted through the drive gear 40, the driven gear 128, the rolling motion transmitting tube 130, the bevel gear 86, and the rotary sleeve 56 to the distal-end working unit 14, thereby rolling the distal-end working unit 14.

The medical manipulator 10 transmits the rotary drive force from the handle 16 to the distal-end working unit 14 mainly through the rolling motion transmitting tube 130, rather than wires and pulleys. Therefore, the distal-end working unit 14 can be rolled in an unlimited angular range. Since the opening and closing drive force transmitter 80, i.e., the pull wire 70 and the pull rod 91, is inserted and disposed in the rolling motion transmitting tube 130, the opening and closing drive force transmitter 80 can transmit the opening and closing drive force to the end effector 12 without being affected by rotation of the rolling motion transmitting tube 130.

The opening and closing drive force transmitter 80 includes a flexible portion, i.e., the pull wire 70, disposed in the articulated joint 17. Therefore, the opening and closing drive force transmitter 80 can transmit the opening and closing drive force to the end effector 12 through a simple structure. The distal-end working unit 14 is thus of a relatively simple mechanism for opening and closing the distal-end working unit 14 and also tilting the distal-end working unit 14 and also for rolling the distal-end working unit 14 in an unlimited angular range.

A mechanism for enabling the distal-end working unit 14 to make a tilting movement will be described below. The handle body 20 houses therein a worm gear 144 rotatable about a vertical axis in response to rotation of the tilting wheel 26 and a rotor assembly 146 rotatable about a transversely horizontal axis of the body section 23 and having a worm wheel 147 held in mesh with the worm gear 144.

The rotor assembly 146 also has a drive pulley 148 coaxially joined to the worm wheel 147 for rotation in unison therewith. The tilting wire 150, which is trained around the drive pulley 148, extends through the shaft 18 into a distal end portion of the shaft 18 where the tilting wire 150 is trained around the driven pulley 90 (see FIG. 5A and the like).

The tilting wire 150 is also trained around a first intermediate pulley 152 and a second intermediate pulley 154 that are disposed in the handle body 20 forwardly of the drive pulley 148, and around a first tension pulley 159 and a second tension pulley 165 that are disposed in the handle body 20 rearwardly of the drive pulley 148. The first tension pulley 159 tensions a portion of the wire 150 between the drive pulley 148 and the driven pulley 90, and the second tension pulley 165 tensions another portion of the wire 150 between the drive pulley 148 and the driven pulley 90.

The shaft 18 and the rolling motion transmitting tube 130 define an annular space defined therebetween which extends axially through the shaft 18. The tilting wire 150 is inserted in the annular space. The tilting wire 150 is trained around the driven pulley 90 that is disposed in the distal end portion of the shaft 18 (see FIG. 5A).

When the user manually turns the tilting wheel 26 shown in FIGS. 1 and 2, the force applied to the tilting wheel 26 is transmitted to the rotor assembly 146, moving the tilting wire 150 trained around the drive pulley 148 of the rotor assembly 146. The movement of the tilting wire 150 is transmitted through a former end of the shaft 18 to the driven pulley 90, which is rotated to tilt the distal-end working unit 14 with respect to the shaft 18.

With the medical manipulator 10 according to the present embodiment, an operating means 21 (see FIG. 5A) for acting on the end effector 12 can be placed substantially centrally in the distal-end working unit 14 because the rotary sleeve 56 (rotor) is hollow, thereby allowing the distal-end working unit 14 to roll in an unlimited angular range. According to the present embodiment, the opening and closing drive force transmitter 80 serves to transmit an opening and closing drive force to the end effector 12 and hence to apply a mechanical action on the end effector 12. Therefore, the opening and closing drive force transmitter 80 operates as the above operating means 21.

Since the rotational support tube 58 is disposed outside, not inside, of the rotary sleeve 56, the space in the rotary sleeve 56 can preferably be used as a space in which the operating means 21 is disposed, and the distal-end working unit 14 can be simplified in structure. According to the present invention, therefore, the medical manipulator 10 has the distal-end working unit 14 that has a large number of degrees of freedom without constitutive complexities.

In the medical manipulator 10, the engaging members 72 are inserted in the side holes 71 formed in the rotational support tube 58 and also inserted in the annular groove 56d in the rotary sleeve 56 within the rotational support tube 58. Accordingly, the engaging members 72 engage in the annular groove 56d in the axial directions. This engaging structure allows the rotary sleeve 56 to rotate relatively to the rotational support tube 58 while preventing the rotary sleeve 56 from axially moving with respect to the rotational support tube 58.

An alternative structure to be described below, though not according to the above embodiment, is also effective to place the rotary sleeve 56 rotatably, but axially immovably, within the rotational support tube 58. According to the alternative structure, the rotational support tube 58 comprises two separate semicircular members (hereinafter referred to as "segment members"), and the rotary sleeve 56 has a circumferentially extending annular ridge on an outer circumferential surface thereof whereas each of the segment members has a circumferentially extending arcuate groove defined in an inner circumferential surface thereof. To assemble the alternative structure, the rotary sleeve 56 is surrounded by the two segment members, with the annular ridge placed in the arcuate grooves, and the segment members are then welded to each other. The rotary sleeve 56 is thus rotatably supported by the inner circumferential surface of the rotational support tube 58. The annular ridge that engages in the arcuate grooves prevents the rotary sleeve 56 from moving axially with respect to the rotational support tube 58.

The rotational support tube 58 in the form of two segment members poses the following problems: The process of forming the arcuate grooves in the inner circumferential surfaces of the segment members tends to involve an increased number of man-hours to achieve a desired machining accuracy. According to a fabrication process, the rotational support tube 58 that has been manufactured as a unitary product is cut into two segment members, and then annular grooves are formed in the respective inner circumferential surfaces of the two segment members, after which the two segment members are welded to each other. If such a fabrication process is employed, then the arcuate shape of the segment members is liable to spread under internal stresses produced when the arcuate grooves were formed, with the result that the segment members tend to find it difficult to keep a desired tubular shape accuracy when combined together. Even if the rotational support tube 58 is manufactured as a unitary product having a desired tubular shape accuracy by a cutting process, the tubular shape accuracy may possibly be lowered because the rotational support tube 58 is thermally deformed when the segment members are welded to each other. The process of welding the segment members requires an increased number of man-hours due to a large length along which the segment members need to be welded. The above fabrication process has many validation elements.

With the medical manipulator 10 according to the present embodiment, however, the rotational support tube 58 is a unitary product, not a component made up of two segment members welded together, and the engaging members 72 are inserted in the side holes 71 formed in the rotational support tube 58 and engage in the annular groove 56d in the rotary sleeve 56 within the rotational support tube 58. This engaging structure, which is free of the process of forming grooves, makes it easier to perform accuracy management and requires a smaller number of manufacturing man-hours than the alternative structure wherein the rotational support tube 58 comprises two segment members with arcuate grooves defined in the inner circumferential surfaces thereof, and the rotary sleeve 56 has an annular ridge on an outer circumferential surface thereof, the annular ridge engaging in the arcuate grooves to prevent the rotary sleeve 56 from moving axially with respect to the rotational support tube 58. The rotational support tube 58 has its tubular shape accuracy maintained appropriately as it is free from deformations due to internal stresses which would otherwise tend to occur if grooves are formed.

According to the present embodiment, furthermore, as there is no welding process required to produce the rotational support tube 58 as a tubular product, its tubular shape accuracy is not lowered due to thermal deformations which would otherwise be caused if welded, and the number of man-hours required to produce the rotational support tube 58 is smaller than if the rotational support tube 58 is made up of two segment members welded together. The structure according to the present embodiment has fewer validation elements.

According to the present embodiment, in particular, since the engaging members 72 are in the form of a pin each, the area of contact between the engaging members 72 and the annular groove 56d is small to lower frictional resistance therebetween, thereby minimizing resistance to the rotation of the rotary sleeve 56 with respect to the rotational support tube 58. Consequently, the rotary sleeve 56 can rotate smoothly with respect to the rotational support tube 58 while at the same time the rotary sleeve 56 is properly prevented from moving axially with respect to the rotational support tube 58.

According to the present embodiment, furthermore, since the engaging members 72 are provided at a plurality of locations that are angularly spaced circumferentially around the rotational support tube 58, the engaging members 72 are highly effective to prevent the rotary sleeve 56 from moving axially with respect to the rotational support tube 58.

The medical manipulator 10 according to the present embodiment is electrically rolled by the motor 38, and manually tilted by the user. However, the medical manipulator 10 may be modified such that it is electrically tilted by the motor 38 and manually rolled by the user. Inasmuch as the medical manipulator 10 is not electrically rolled and tilted, but is either rolled or tilted by a drive source, the medical manipulator 10 requires a single drive source and hence is smaller in size and weight than if the medical manipulator 10 is electrically rolled and tilted.

According to still another modification, one or two or more rolling, tilting, and opening and closing movements of the medical manipulator 10 may be electrically controlled, or the medical manipulator 10 may be rolled, tilted, and opened and closed all manually.

Second Embodiment

Figure 7:
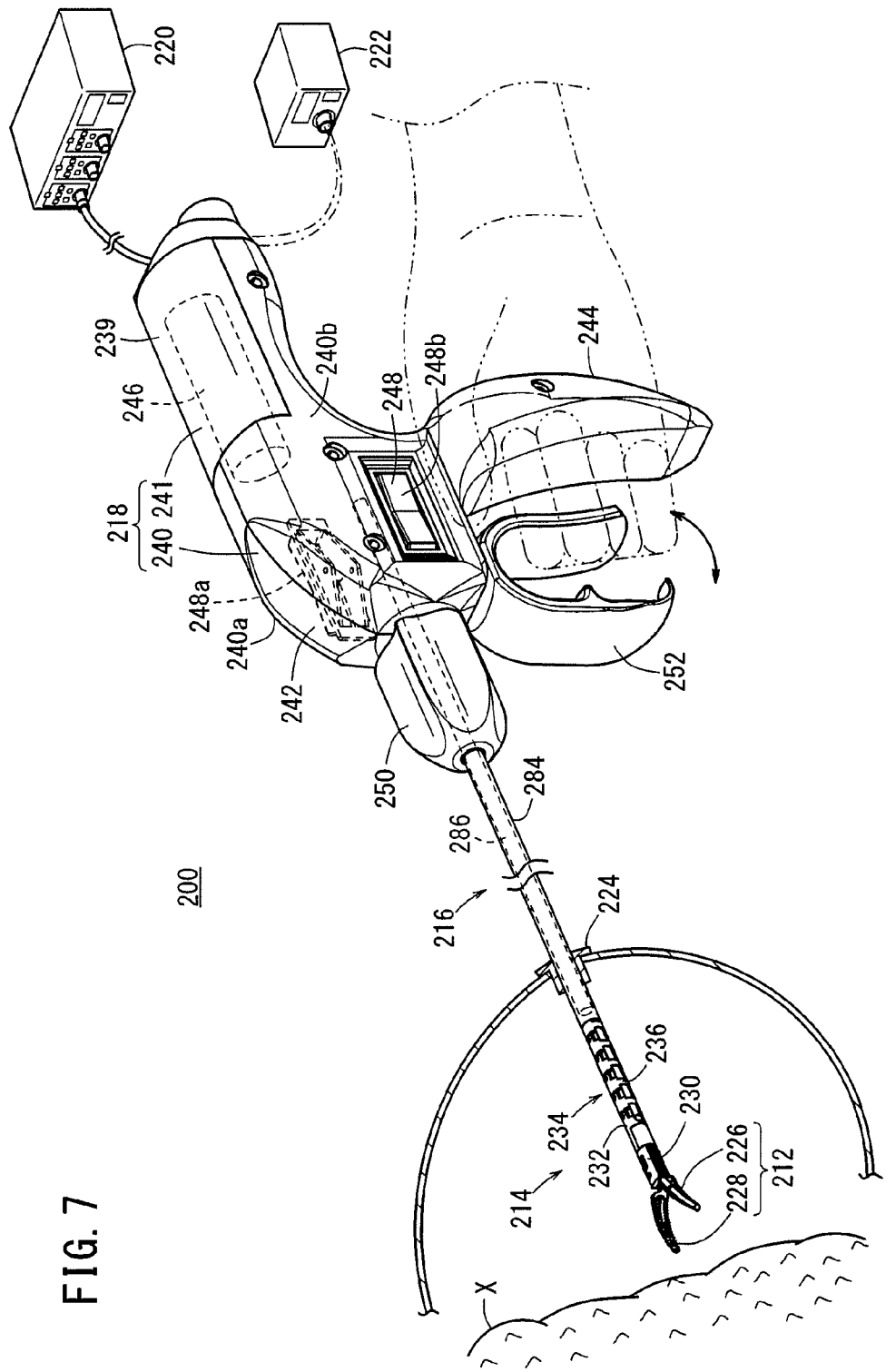
FIG. 7 is a perspective view, partly omitted from illustration, of a medical manipulator according to a second embodiment of the present invention.

FIG. 7 shows in perspective, partly omitted from illustration, a medical manipulator 200 according to a second embodiment of the present invention. The medical manipulator 200 is used in surgical techniques in endoscopic surgical operations, for example, to treat, e.g., cauterize by heating, a biological tissue as an object X to be treated. The biological tissue as the object X to be treated may be a tumor (lesion), a muscle, a blood vessel, a nerve, or the like, for example. The medical manipulator 200 has an end effector 212 (electrosurgical scalpel) which grips a biological tissue and supplies an electric current to the biological tissue.

As shown in FIG. 7, the medical manipulator 200 has a distal-end working unit 214 including the end effector 212 for treating a biological tissue, a shaft 216 connected to the proximal end of the distal-end working unit 214 and extending over a predetermined length of about 350 mm, for example, toward the proximal end of the medical manipulator 200, and a handle 218 disposed on the proximal end of the shaft 216 for actuating the distal-end working unit 214 based on an action (input) from the user of the medical manipulator 200. The handle 218 is electrically connected to a controller 220 for supplying electric power to the medical manipulator 200 to actuate the distal-end working unit 214 and a high-frequency power supply 222 for supplying a high-frequency electric current to the end effector 212.

When the medical manipulator 200 is in use, the user, i.e., a surgical practitioner such as a surgeon or the like, grips and operates the handle 218 to insert the distal-end working unit 214 on the distal end of the medical manipulator 200 and the shaft 216 through a trocar 224 into the body cavity of the patient. With the distal end of the medical manipulator 200 being inserted in the body cavity, the user changes the posture of the end effector 212 and opens and closes the end effector 212 while monitoring the end effector 212 and the biological tissue through an endoscope, not shown, and moves the end effector 212 to reach the biological tissue and supplies an electric current to the biological tissue.

The end effector 212 is not limited to an electrosurgical scalpel for supplying an electric current to the biological tissue, but may be any of various surgical instruments. For example, the end effector 212 may be a pair of scissors or a scalpel (blade) for cutting the biological tissue, or may be a gripping instrument for gripping a medical tool such as a pair of forceps, a needle, or the like and controlling the gripped medical tool to treat the biological tissue.

The distal-end working unit 214 that includes the end effector 212 may have its posture changed with respect to the shaft 216 with a plurality of degrees of freedom. According to the present embodiment, the distal-end working unit 214 can change its posture by being tilted (swung) to the left or right from the axis of the shaft 216 and also by being rolled about the longitudinal axis of the end effector 212. In the present embodiment, when the distal-end working unit 214 is tilted, it actually yaws, i.e., swings, to the left or right from the axis of the shaft 216. However, the distal-end working unit 214 may pitch or swing upwardly or downwardly, instead of yawing to the left or right.

The shaft 216 whose distal end is coupled to the distal-end working unit 214 extends straight and has its proximal end portion connected to the handle 218. The shaft 216 is in the form of a long slender tubular member. The shaft 216 houses a plurality of members inserted and disposed in its space which make up a power transmitting mechanism for transmitting mechanical power required for opening and closing the end effector 212 and for tilting and rolling the distal-end working unit 214 from the handle 218 to the distal-end working unit 214. While the user is practicing a surgical technique, the proximal end of the shaft 216 protrudes out of the body of the patient, and the user controls the handle 218 to adjust the position and angle of the medical manipulator 200, thereby changing the angle at and the depth through which the distal-end working unit 214 and the shaft 216 are inserted in the body cavity.

The handle 218 has a handle body 240 housing a plurality of operating units therein and shaped like a pistol so that it can easily be gripped by one hand of the user, and a drive unit 241 including a motor 246. The drive unit 241 is removably mounted on the handle body 240. When the motor 246 of the drive unit 241 mounted on the handle body 240 is energized, the drive power generated by the motor 246 is transmitted to the distal-end working unit 214. The handle body 240, the shaft 216, and the distal-end working unit 214 jointly make up a manipulator assembly. After the medical manipulator 200 has been used a predetermined number of times, the manipulator assembly may be removed from the drive unit 241 and discarded, and a new manipulator assembly may be connected to the drive unit 241. Therefore, the drive unit 241 is reusable in combination with a plurality of manipulator assemblies.

The handle body 240 includes a body section 242 and a grip 244 extending downwardly from the body section 242. The handle body 240 has a casing that houses therein a number of drive components including gears, links, etc. for moving the distal-end working unit 214, i.e., tilting, rolling, and opening and closing the distal-end working unit 214 as described above. The body section 242 supports thereon a trigger 252 (opening and closing member) for opening and closing the end effector 212, a switch 248 (tilting member) for tilting, and a rotary handle 250 (rolling member) for rolling.

According to the present embodiment, the trigger 252 is constituted as a manual operating member. When the user operates the trigger 252, the manual operating force applied by the user is mechanically transmitted from the trigger 252 to the end effector 212 of the distal-end working unit 214, opening or closing the end effector 212. Specifically, when the user moves the trigger 252 forwardly, the end effector 212 is opened, and when the user moves the trigger 252 rearwardly, the end effector 212 is closed.

According to the present embodiment, the switch 248 is constituted as an electric operating member for applying an operation command to the motor 246 through the controller 220. The switch 248 has a right switch 248a and a left switch 248b. The right and left switches 248a, 248b have respective central portions supported on the handle body 240 and opposite end portions (distal and proximal end portions) displaceable about the central portions by being pushed by the user. When the user presses the right switch 248a or the left switch 248b, a signal depending on the position where the right switch 248a or the left switch 248b is pressed is transmitted to the controller 220. Based on the transmitted signal, the controller 220 energizes the motor 246 to generate a drive force, which is transmitted to the distal-end working unit 214, tilting the distal-end working unit 214 in a direction (leftward or rightward direction or upward or downward direction) not parallel to the axis of the shaft 216.

The rotary handle 250 is mounted on the distal end of the body section 242. The rotary handle 250 is constituted as a manual operating member. When the user rotates the rotary handle 250, the manual operating force applied by the user is mechanically transmitted through a tilting power transmitting system in the handle 218 and the shaft 216 to the distal-end working unit 214, turning the distal-end working unit 214 about the longitudinal axis thereof.

The drive unit 241 includes a housing 239, the motor 246 which is disposed in the housing 239, and a pinion gear, not shown, fixed to the output shaft of the motor 246. The drive unit 241 is removably mounted on a rear end of the handle body 240. The controller 220 and the high-frequency power supply 222 are electrically connected to the drive unit 241. The controller 220, which supplies electric power to the motor 246 and controls the motor 246 to operate, is supplied with electric power from an external power supply. When the user operates the switch 248, the switch 248 transmits a signal depending on the operation of the switch 248 to the controller 220, which controls the motor 246 to operate. The function of the controller 220 may be partly or wholly incorporated in the drive unit 241. The high-frequency power supply 222 has a function to supply electric power (high-frequency electric power) to the end effector 212 based on an action taken by the user.

Figure 8:
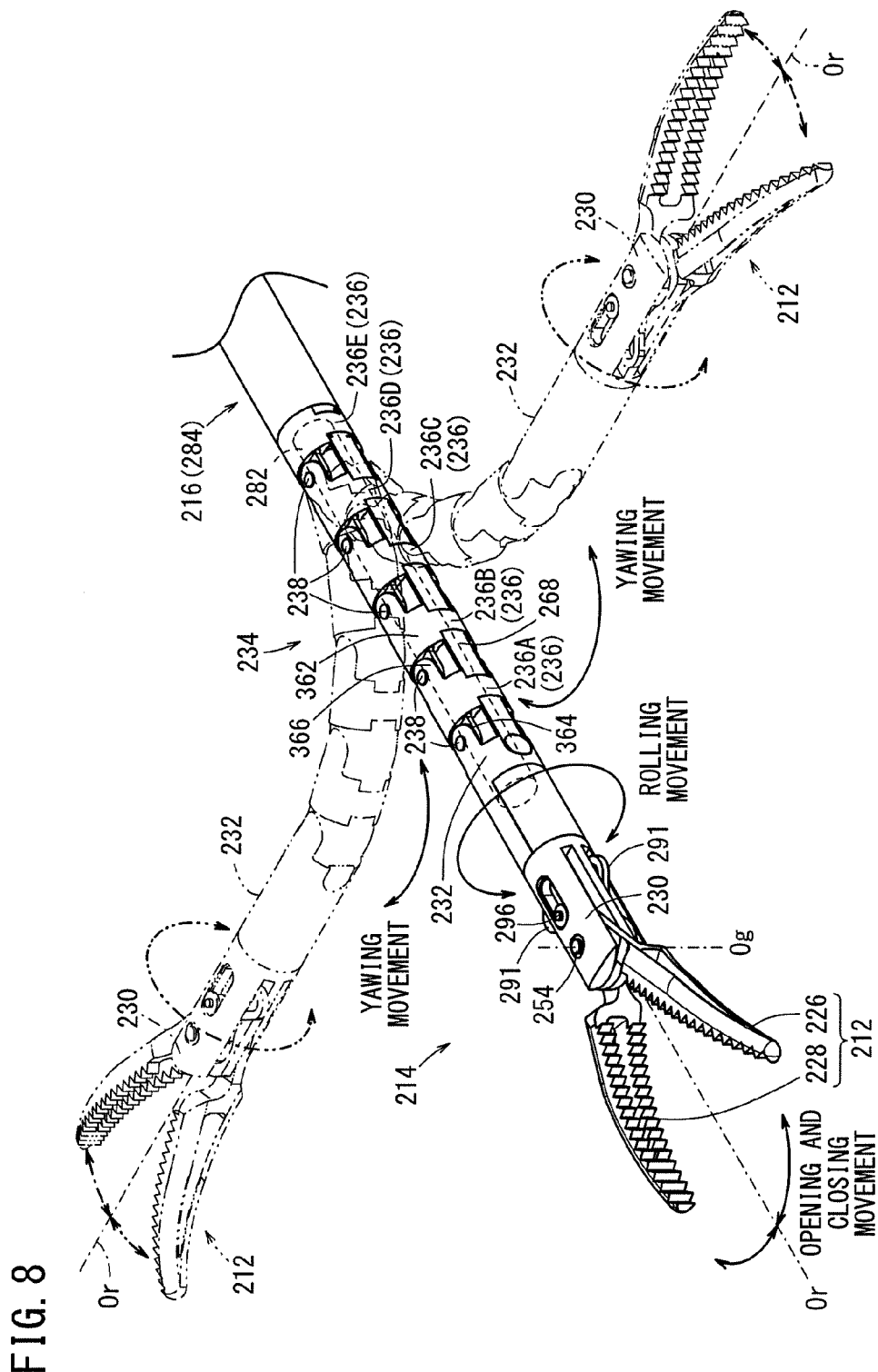
FIG. 8 is an enlarged perspective view of a distal-end working unit of the medical manipulator shown in FIG. 7.
Figure 9:
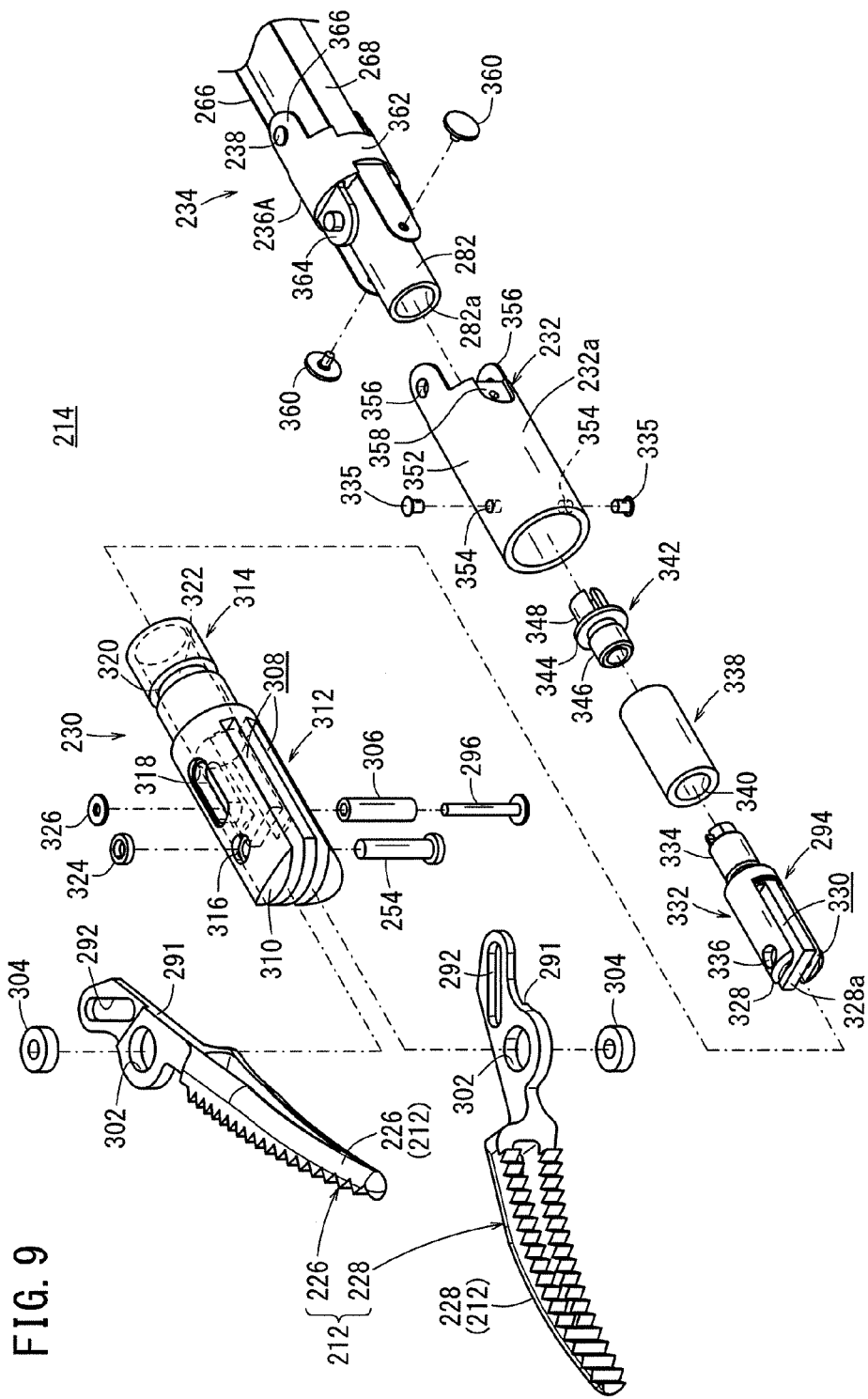
FIG. 9 is an enlarged and exploded perspective view of the distal-end working unit of the medical manipulator shown in FIG. 7.
Figure 10:
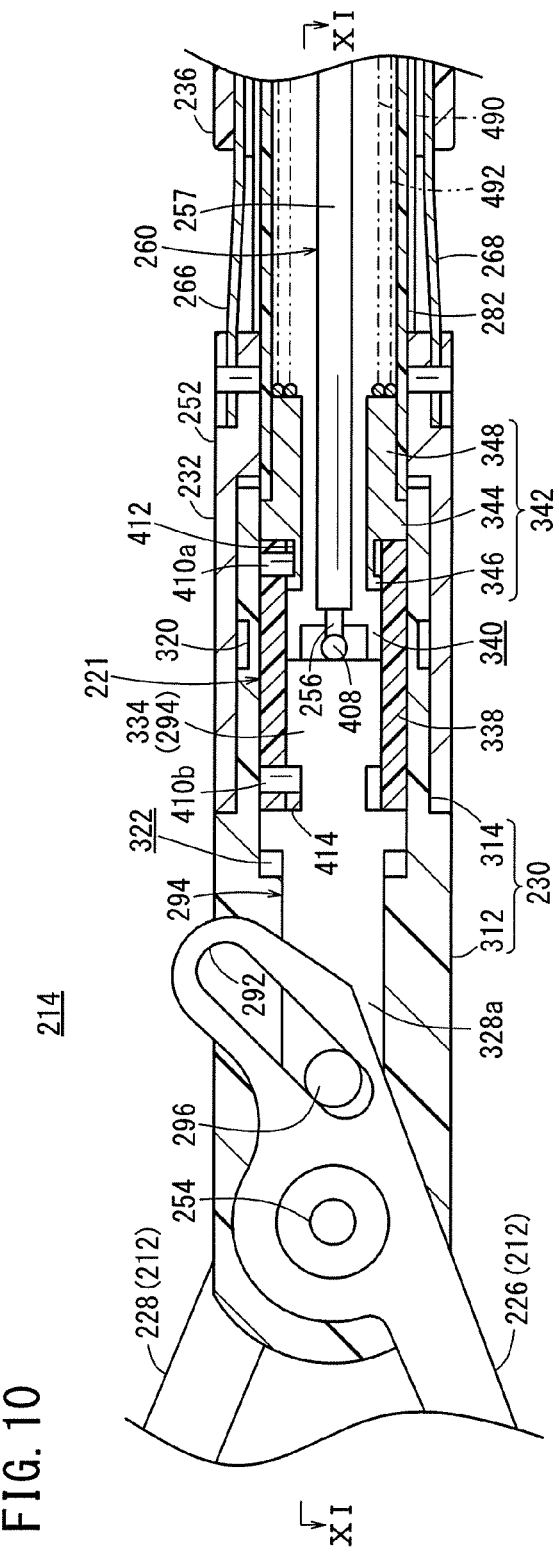
FIG. 10 is a vertical cross-sectional view of the distal-end working unit of the medical manipulator shown in FIG. 7.
Figure 11A:
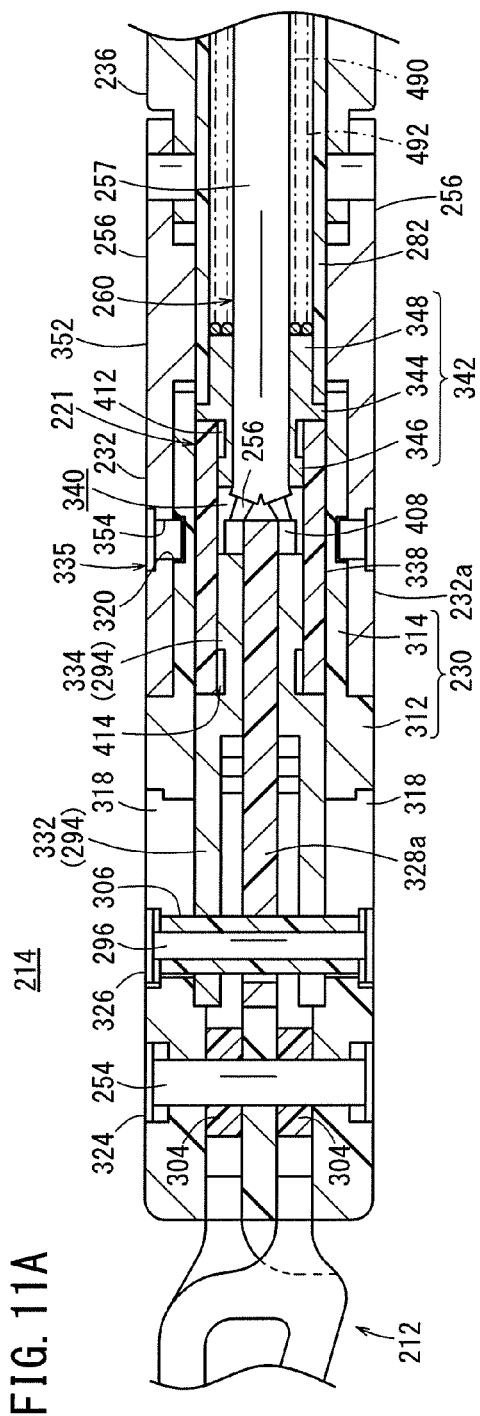
FIG. 11A is a vertical cross-sectional view taken along line XI-XI of FIG. 10.

FIG. 8 shows the distal-end working unit 214 in enlarged perspective. FIG. 9 shows the distal-end working unit 214 in exploded perspective. FIG. 10 shows in vertical cross section the distal-end working unit 214. FIG. 11A is a vertical cross-sectional view taken alone line XI-XI of FIG. 10. As shown in FIGS. 8 to 11A, the distal-end working unit 214 includes an end effector 212 that can be opened and closed, a gripper holder 230 (rotor) to which the end effector 212 is fixed, a rotational support tube 232 by which the gripper holder 230 is rotatably supported for rotation about its own axis, a bendable shank 234 that is bendable between the rotational support tube 232 and the shaft 216, and a hollow tube 282 disposed in the bendable shank 234.

The end effector 212 has a first gripper 226 and a second gripper 228. The first gripper 226 and the second gripper 228 are rotatably coupled to each other by a pivot pin 254 for rotation about a gripper axis Og (see FIG. 8) aligned with the pivot pin 254.

As shown in FIGS. 9 and 11A, extensions 291 have respective circular holes 302 formed therein near distal ends thereof. The pivot pin 254 is fitted in the circular holes 302 and supported by insulation rings 304 that are fitted in the circular holes 302. The extensions 291 also have respective oblong holes 292 formed therein near proximal ends thereof. A movable pin 296 inserted in an insulation sleeve 306 is inserted in the oblong holes 292.

The gripper holder 230 has two slots 308 defined in a distal end and side surfaces thereof and extending parallel to each other along the longitudinal directions thereof. The first gripper 226 and the second gripper 228 are pivotally supported by the pivot pin 254 with the extensions 291 inserted in the respective slots 308. The gripper holder 230 has a proximal end portion rotatably inserted in the rotational support tube 232 that is in the form of a hollow cylinder.

The gripper holder 230 has a gripper-side trifurcated member 312 having three holder plates 310 extending to the distal end thereof with the slots 308 defined between the three holder plates 310, and an engaging tube 314 joined to the proximal end of the gripper-side trifurcated member 312 and extending to the proximal end of the gripper holder 230.

The gripper-side trifurcated member 312 has a pivot pin hole 316 formed in the three holder plates 310 near their distal ends. While the proximal end portions of the first and second grippers 226, 228 are disposed in the slots 308, the pivot pin 254 is inserted in the pivot pin hole 316 and has an end fixed to a washer 324. The gripper-side trifurcated member 312 also has a movable pin oblong hole 318 for receiving both ends of the movable pin 296 therein, formed therein more closely to the proximal end thereof than the pivot pin hole 316. The movable pin 296 is inserted in the oblong holes 292 formed in the first and second grippers 226, 228 and the movable pin oblong hole 318 formed in the gripper holder 230, and is movable along the oblong holes 292, 318. A washer 326 is fixed to an end of the movable pin 296.

The engaging tube 314 has an annular groove 320 defined in an outer circumferential surface thereof and extending through 360°. The gripper-side trifurcated member 312 and the engaging tube 314 have a sliding space 322 (see FIG. 10) defined jointly therein with a movable body 294 inserted therein.

The rotational support tube 232 has a tubular member 232a in the form of a hollow cylinder. The gripper holder 230 is rotatably supported on an inner circumferential surface of the tubular member 232a. As shown in FIGS. 11A and 11B, the rotational support tube 232 has side holes 354 formed therein that extend between inside and outside areas of the rotational support tube 232. In the illustrated embodiment, the side holes 354 are in the form of circular pin holes extending radially through the wall of the tubular member 232a of the rotational support tube 232. However, the side holes 354 may be in the form of oblong holes extending circumferentially through a predetermined angle. In the illustrated embodiment, the rotational support tube 232 has two side holes 354 disposed diametrically opposite to each other across the axis of the rotational support tube 232. However, the rotational support tube 232 may have a single side hole or three or more side holes angularly spaced at intervals in the circumferential directions.

Engaging members 335 are disposed in the respective side holes 354. Specifically, the engaging members 335 are inserted in the respective side holes 354 and fixed to the rotational support tube 232. In the illustrated embodiment, the engaging members 335 have outer ends 335a, i.e., ends near the rotational support tube 232, firmly secured to the rotational support tube 232 by an appropriate joining process such as welding, adhesive bonding, or the like, for example. The engaging members 335 have inner ends 335b, i.e., ends near the gripper holder 230, projecting inwardly from the inner circumferential surface of the rotational support tube 232 and inserted in the annular groove 320 defined in the gripper holder 230. Each of the engaging members 335 is in the form of a pin. The outside diameter R2 of the inner end 335b is substantially the same as or slightly smaller than the width W2 of the annular groove 320, i.e., the dimension of the angular groove 320 along the axis of the gripper holder 230.

Each of the engaging members 335 is not limited to a pin shape, but may be of an arcuate shape extending in a predetermined angular range in the circumferential directions of the rotational support tube 232, for example.

The outer end 335a of each of the engaging members 335 has an annular flange 335c disposed in an annular large-diameter portion 354a in the outer end of one of the side holes 354. The engaging members 335 are thus accurately positioned with respect to the rotational support tube 232, and project from the inner circumferential surface of the rotational support tube 232 by a desired distance. If a small clearance is present between the inner end 335b of the engaging member 335 and the bottom of the annular groove 320, as illustrated, then it effectively reduces the sliding resistance between the engaging member 335 and the annular groove 320.

The engaging members 335 fixed to the rotational support tube 232 engage in the annular groove 320 defined in the gripper holder 230. Therefore, the gripper holder 230 and the rotational support tube 232 are operatively coupled to each other such that the gripper holder 230 is rotatable, but axially immovable, with respect to the rotational support tube 232. The gripper holder 230 is prevented from being dislodged from the rotational support tube 232 by the engaging members 335 engaging in the annular groove 320.

The distal-end working unit 214 is assembled by successively performing a process (inserting process) of inserting the proximal end of the gripper holder 230 into the rotational support tube 232 from its distal end, a process (engaging member placing process) of inserting the engaging members 335 into the respective side holes 354 formed in the rotational support tube 232 from outside of the rotational support tube 232 and placing the inner ends 335b of the engaging members 335 in the annular groove 320 of the gripper holder 230, and a process (joining process) of jointing the rotational support tube 232 and the engaging members 335 by welding, adhesive bonding, or the like, for example. The gripper holder 230 is thus rotatably supported by the inner circumferential surface of the rotational support tube 232 while at the same time the gripper holder 230 is prevented from being dislodged from the rotational support tube 232.

Figure 11C:
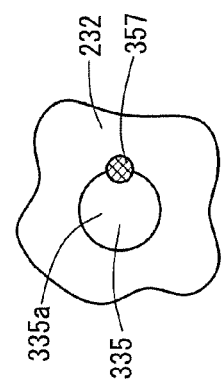
FIG. 11C is a view showing a joint between the engaging member and a rotational support tube.
Figure 11B:
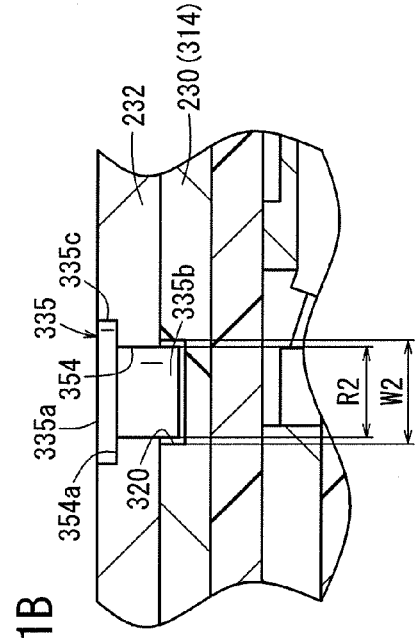
FIG. 11B is a vertical cross-sectional view of an engaging member and its peripheral parts of the distal-end working unit.

If the rotational support tube 232 and the engaging members 335 are joined to each other by welding, then each of the engaging members 335 may be joined to the rotational support tube 232 by a single joint 357 (welded region), as shown in FIG. 11C in which the engaging member 335 is viewed from the outer end 335a. Since there is almost no load applied in a direction to pull the engaging member 335 from the side hole 354, the single joint 357 formed between each engaging member 335 and the rotational support tube 232 is enough to provide a sufficient joining strength. Therefore, even though the rotational support tube 232 and the engaging members 335 are joined to each other by welding, the rotational support tube 232 is not liable to be thermally deformed by the welding process and keeps a high dimensional accuracy for its hollow cylindrical shape.

The engaging members can be in form of a screw having an outer thread screwed into a corresponding thread in the side hole. This facilitates a disassembling of rotor and rotational support tube.

The movable body 294 movable back and forth with respect to the gripper holder 230 is disposed in the gripper holder 230. The movable pin 296 is fixed to the movable body 294. When the end effector 212 is rolled, the gripper holder 230 and the movable body 294 rotate together with each other. When the end effector 212 is opened and closed, the gripper holder 230 does not move, but the movable body 294 move back and forth in the gripper holder 230.

As shown in FIG. 9, the movable body 294 has, as is the case with the gripper holder 230, a movable-body-side trifurcated member 332 having three holder plates 328 extending to the distal end thereof with slots 330 defined between the three holder plates 328, and an insert 334 joined to the proximal end of the movable-body-side trifurcated member 332 and extending to the proximal end of the movable body 294. The movable-body-side trifurcated member 332 has a movable pin circular hole 336 formed therein closely to the distal ends of the three holder plates 328. The movable pin 296 is inserted in the movable pin circular hole 336.

Of the three holder plates 328 of the movable body 294, a central holder plate 328a is made of an insulation material. As shown in FIG. 11A, the holder plate 328a extends through the insert 334 and has its proximal end portion projecting from the proximal end of the insert 334. The proximal end portion of the holder plate 328a which projects from the proximal end of the insert 334 has upper and lower surfaces with welding pads 408 disposed thereon. Metal wires 256 protruding from the distal end portion of a conductive cable 260 are welded to the welding pads 408 by a welding material. The conductive cable 260, which has a distal end portion fixedly held by a connector 342, extends axially through the hollow tube 282.

A tube 338 in the form of a hollow cylinder is disposed in the engaging tube 314 of the gripper holder 230, axially movably with respect to the engaging tube 314. The tube 338 has a length of about 6 mm. The insert 334 of the movable body 294 is inserted in a distal end portion of the tube 338. The connector 342 is inserted in a proximal end portion of the tube 338.

As shown in FIG. 10, connector pins 410a, 410b are mounted respectively on the proximal and distal end portions of the tube 338 and project radially inwardly from an inner circumferential surface of the tube 338. The connector pin 410b on the distal end portion of the tube 338 has an inner end inserted in a movable-body-side engaging groove 414 defined in the insert 334 of the movable body 294. The connector pin 410a on the proximal end portion of the tube 338 has an inner end inserted in a connector-side engaging groove 412 defined in the connector 342. The connector 342, the tube 338, and the movable body 294 are thus axially connected to each other by the connector pins 410a, 410b. Therefore, a force for axially moving the movable body 294 back and forth is reliably transmitted from the hollow tube 282 through the tube 338 to the movable body 294.

The connector 342, which is in the form of a hollow cylinder, is connected to the proximal end of the tube 338. The connector 342 includes a flange 344 disposed in a longitudinally central position, a distal-end joint protrusion 346 extending from the flange 344 to the distal end thereof, and a proximal-end joint protrusion 348 extending from the flange 344 to the proximal end thereof. The connector 342 has the distal-end joint protrusion 346 inserted in the tube 338 and the proximal-end joint protrusion 348 inserted in the hollow tube 282, interconnecting the tube 338 and the hollow tube 282.

The hollow tube 282 that has a space 282a (see FIG. 9) extending axially therethrough and that is flexible enough to follow the bendable shank 234 as it bends is connected to the proximal end of the connector 342. The hollow tube 282 is disposed in the bendable shank 234 and has its proximal end coupled and fixed to an inner tube 286 (see FIG. 12) of the shaft 216. The hollow tube 282 has a function as a rotatable torque tube even when it bends with the bendable shank 234. The hollow tube 282 has an inside diameter of about 1.5 mm, for example.

In the distal-end working unit 214 thus constituted, when the hollow tube 282 is axially moved, its movement is transmitted through the connector 342 and the tube 338 to the movable body 294. When the movable body 294 moves forwardly in the gripper holder 230 until the movable pin 296 reaches a position at the distal ends of the oblong holes 292, the extensions 291 of the first and second grippers 226, 228 cross each other at the movable pin 296, the distal end portions of the first and second grippers 226, 228 are spaced apart from each other, opening the end effector 212. When the movable body 294 moves rearwardly in the gripper holder 230 until the movable pin 296 reaches a position at the proximal ends of the oblong holes 292, the movable pin 296 guides the oblong holes 292 in the first and second grippers 226, 228 to bring the extensions 291 together into overlapping relation to each other, whereupon the distal end portions of the first and second grippers 226, 228 are brought together, closing the end effector 212. Therefore, the end effector 212 is opened and closed when forces toward the distal and proximal ends are transmitted from the hollow tube 282 thereto. The end effector 212 can be opened and closed at desired timing based on an action taken by the user irrespectively of any change in the posture of the end effector 212.

Figure 12:
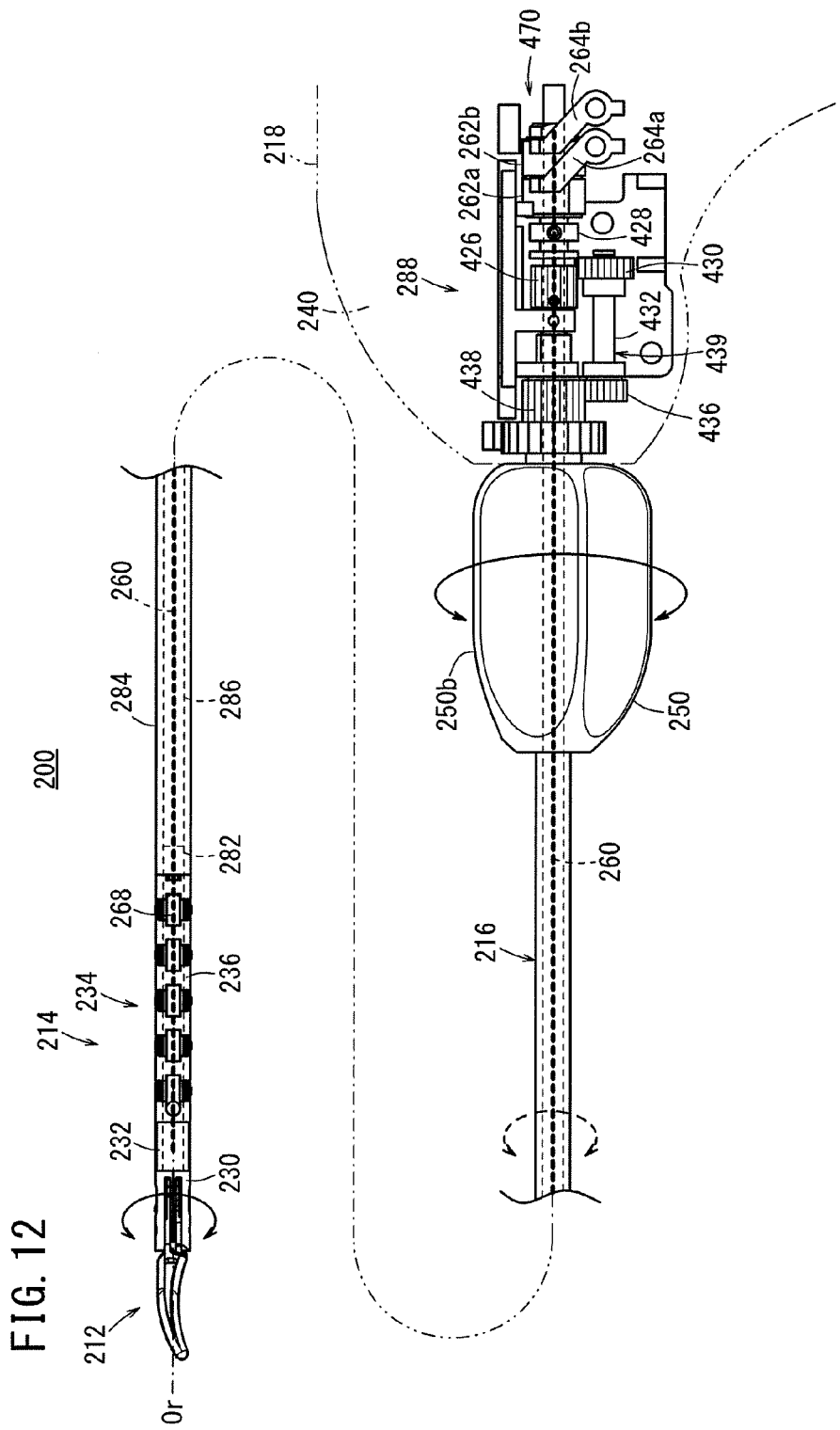
FIG. 12 is a side view showing a mechanism for rolling the medical manipulator shown in FIG. 7

As shown in FIG. 12, the shaft 216 that is connected to the bendable shank 234 is of a double-walled structure having an outer tube 284 and the inner tube 286 disposed in the outer tube 284. The inner tube 286 is axially movable in the outer tube 284 and rotatable about its own axis. The proximal end of the hollow tube 282 and the distal end of the inner tube 286 are relatively non-rotatably coupled to each other. When the inner tube 286 is axially moved in the outer tube 284, the hollow tube 282 is axially moved in the bendable shank 234. When the inner tube 286 is rotated about its own axis in the outer tube 284, the hollow tube 282 is rotated in the bendable shank 234.

A back-and-forth moving mechanism, not shown, which is disposed in the handle 218 is connected to the proximal end of the inner tube 286. The back-and-forth moving mechanism has a plurality of links that mechanically connect the inner tube 286 and the trigger 252 (see FIG. 7) to each other. When the user manually pulls the trigger 252, the trigger 252 transmits its operating force into the handle 218, causing the back-and-forth moving mechanism to move the inner tube 286 toward the proximal end thereby to move the hollow tube 282 toward the proximal end. When the user manually pushes the trigger 252, the trigger 252 transmits its operating force into the handle 218, causing the back-and-forth moving mechanism to move the inner tube 286 toward the distal end thereby to move the hollow tube 282 toward the distal end.

The hollow tube 282 has an axial length greater than the bendable shank 234 of the distal-end working unit 214, such that the hollow tube 282 will overlap the bendable shank 234 at all times when the hollow tube 282 is moved back and forth. When the bendable shank 234 is bent and the hollow tube 282 is also bent therewith, the hollow tube 282 can move along the bent hollow tube 282, transmitting its force of back-and-forth movement to the tube 338 that is connected to the distal end of the hollow tube 282.

The medical manipulator 200 has a function to supply an electric current to a biological tissue when the end effector 212 grips the biological tissue. The first and second grippers 226, 228 shown in FIG. 7 or the like are made of an electrically conductive material, and are constituted as electrodes, i.e., a positive electrode and a negative electrode, for supplying an electric current to a biological tissue. In other words, the end effector 212 according to the present embodiment serves as a bipolar electrosurgical scalpel. However, the end effector 212 is not limited to a bipolar electrosurgical scalpel, but may be a monopolar electrosurgical scalpel.

As shown in FIGS. 10 and 11A, the conductive cable 260 is connected to the proximal end of the movable body 294. The conductive cable 260 comprises two metal wires 256, which are made of copper, for example, and an insulating member 257 covering the two metal wires 256. The conductive cable 260 and the shaft 216 extend toward the proximal end and are inserted in the handle 218. According to the present embodiment, the conductive cable 260 is disposed to extend axially in the hollow tube 282 and the inner tube 286. Since the conductive cable 260 does not need to be placed on side surfaces of the distal-end working unit 214 and the shaft 216, the conductive cable 260 is prevented from becoming entangled as the distal-end working unit 214 operates, and can supply an electric current well.

As shown in FIG. 11A, the first gripper 226 and the second gripper 228 are pivotally supported by the single pivot pin 254 that are supported by the insulation rings 304. When an operating force for opening or closing the end effector 212 is applied, the distal end portions of the first gripper 226 and the second gripper 228 are displaced toward or away from each other about the pivot pin 254. When the end effector 212 is opened with the distal end portions of the first gripper 226 and the second gripper 228 being spaced from each other, no electric current flows between the first gripper 226 and the second gripper 228. However, when the end effector 212 is closed with the distal end portions of the first gripper 226 and the second gripper 228 abutting against each other, and also when the end effector 212 is essentially closed with the biological tissue sandwiched between the first gripper 226 and the second gripper 228, an electric current flows between the first gripper 226 and the second gripper 228 and through the biological tissue.

When the end effector 212 is closed, as described above, an electric current flows between the first gripper 226 and the second gripper 228, which are of different polarities, that are connected to each other. Specifically, when the biological tissue is sandwiched between the first gripper 226 and the second gripper 228, the high-frequency power supply 222 supplies a high-frequency current through the conductive cable 260 to the first and second grippers 226, 228 and the biological tissue sandwiched therebetween, treating the biological tissue, e.g., cauterizing the biological tissue by heating.

As shown in FIG. 12, the handle body 240 houses therein a slip ring system 470 for continuously keeping the conductive cable 260 and the high-frequency power supply 222 electrically connected when the inner tube 286 is rotating. The slip ring system 470 includes a pair of rotary terminals 262a, 262b fixed to the inner tube 286 of the shaft 216 in the handle body 240, and a pair of contact terminals 264a, 264b held in contact with the rotary terminals 262a, 262b, respectively.

The rotary terminals 262a, 262b are electrically connected respectively to the two metal wires 256 of the conductive cable 260. The rotary terminals 262a, 262b are rotatable in unison with the inner tube 286. The contact terminals 264a, 264b are fixedly positioned in the handle 218, and are electrically connected to the high-frequency power supply 222, which is disposed outside of the handle 218 (see FIG. 7). When the rotary terminals 262a, 262b are rotating, the rotary terminals 262a, 262b are maintained in contact with the contact terminals 264a, 264b, making it possible for the slip ring system 470 to supply high-frequency output electric power from the high-frequency power supply 222 through the conductive cable 260 to the end effector 212.

As shown in FIGS. 10 and 11A, first and second coils 490, 492 which are wound in different directions are disposed in the hollow tube 282 in concentrically superposed relation to each other. The first and second coils 490, 492 are capable of transmitting a rotational torque to the distal end, i.e., the end effector 212, even when the hollow tube 282 is rotated while being bent by the bendable shank 234.

The distal-end working unit 214 is rolled when the gripper holder 230 is rotated with respect to the rotational support tube 232. The rotational support tube 232 is non-rotatably coupled to the bendable shank 234, and the gripper holder 230 is rotatable with respect to the rotational support tube 232. The end effector 212 is thus rotatable in unison with the gripper holder 230.

As shown in FIG. 12, the inner tube 286 projects toward the proximal end more than the outer tube 284, and is rotatably supported by a rotating mechanism 288 that is housed in the handle 218. The handle body 240 includes a drive gear 438 fixed to the proximal end of the rotary handle 250 for rotation in unison therewith, a driven gear 426 fixed to the inner tube 286 for rotation in unison therewith, and an intermediate drive shaft 439 for transmitting drive power between the drive gear 438 and the driven gear 426. The intermediate drive shaft 439 has a first intermediate gear 436 on one end thereof which is held in mesh with the drive gear 438, a second intermediate gear 430 on the other end thereof which is held in mesh with the driven gear 426, and a joint shaft 432 interconnecting the first intermediate gear 436 and the second intermediate gear 430. The intermediate drive shaft 439 is rotatably supported in the handle body 240.

When the user manually rotates the rotary handle 250, the manual operating force (rotational drive force) applied by the user is transmitted through the drive gear 438, the intermediate drive shaft 439, and the driven gear 426 to the inner tube 286. The rotational drive force transmitted to the inner tube 286 is transmitted to the hollow tube 282. As a result, the gripper holder 230 and the end effector 212 that are connected to the distal end of the hollow tube 282 are rotated about the roll axis Or (see FIG. 8). In this manner, the distal-end working unit 214 makes a rolling movement. At this time, the movable body 294, the tube 338, the connector 342, and the conductive cable 260 also rotate in unison with the gripper holder 230.

The inner tube 286 is rotatable unlimitedly with respect to the outer tube 284. The hollow tube 282 that is disposed in a position superposed on the bendable shank 234 is also rotatable unlimitedly. The gripper holder 230 and the end effector 212 are also rotatable unlimitedly. Since the conductive cable 260 extends through the hollow tube 282 and the inner tube 286, the conductive cable 260 is rotatable in unison with the hollow tube 282 and the inner tube 286. Consequently, the medical manipulator 200 has an unlimited range in which the distal-end working unit 214 can be rolled, i.e., the end effector 212 can be rotated. Therefore, the end effector 212 can have its posture variable by its rolling movement as many times as desired.

The medical manipulator 200 is tilted by the bendable shank 234 that is coupled to the proximal end of the rotational support tube 232. The bendable shank 234 comprises a plurality of (five in FIG. 12) joint members 236, each made of a hard material, which are arranged in an axial array.

As shown in FIGS. 8 and 9, of the five joint members 236A to 236E (collectively denoted by 236) of the bendable shank 234, the four joint members 236A through 236D each have a central tube 362 (tube) which is of a tubular shape, a pair of diametrically opposite upper and lower distal-end hinges 364 extending from the central tube 362 toward the proximal lend, and a pair of diametrically opposite upper and lower proximal-end hinges 366 extending from the central tube 362 toward the proximal end.

The distal-end hinges 364 are positioned more radially inwardly than the proximal-end hinges 366. Adjacent ones of the joint members 236 are rotatably coupled to each other by a hinge shaft 238 extending through the distal-end hinges 364 and the proximal-end hinges 366 that overlap each other. As shown in FIGS. 9 and 11A, the rotational support tube 232 has a proximal-end tube 352 having a pair of diametrically opposite upper and lower hinges 356 projecting toward the joint member 236A on the most distal end. These hinges 356 are rotatably coupled to the respective distal-end of the joint member 236A.

The joint member 236E on the most proximal end of the bendable shank 234 is fixedly coupled to the distal end portion of the shaft 216. As with the joint members 236A to 236D, the joint member 236E has a central tube 362 and a pair of diametrically opposite upper and lower distal-end hinges 364, but is free of a pair of diametrically opposite upper and lower proximal-end hinges 366 on the proximal end side of the central tube 362. The joint member 236E has its proximal end fitted in and fixed to the outer tube 284.

A pair of belts, i.e., a first belt 266 and a second belt 268, are disposed respectively on both sides of the axial array of the five joint members 236 along the bendable shank 234. Each of the joint members 236 holds the first and second belts 266, 268 disposed slidably thereon. As shown in FIG. 9, the first and second belts 266, 268 have respective distal end portions fitted in respective cutouts 358 defined in the proximal-end tube 352 and secured by fixing pins 360.

When the motor 246 is energized in the medical manipulator 200, the drive force generated thereby is transmitted through the tilting power transmitting system in the handle 218 and the shaft 216 to the first and second belts 266, 268, which move axially in opposite directions along the bendable shank 234. Therefore, the rotational support tube 232 and the joint members 236A through 236D are tilted through substantially the same angles, respectively, bending the bendable shank 234 to the right or the left.

The tilting power transmitting system may comprise a rack-and-pinion mechanism for converting rotary motion of the motor 246 to linear motion. Alternatively, the tilting power transmitting system may comprise a mechanism including pulleys, belts, wires, etc. The bendable shank 234 may incorporate one or three or more belts, rather than the two belts.

As described above, the medical manipulator 200 according to the present embodiment can roll the end effector 212 in an unlimited angular range by transmitting the rotary drive force from the handle 218 to the end effector 212 through the flexible hollow tube 282 disposed in the bendable shank 234. Therefore, the posture (angle) about the roll axis Or of the end effector 212 at the distal end of the bendable shank 234 can freely be varied to change the orientation of the end effector 212 to match a biological tissue to be treated as many times desired for treating the biological tissue appropriately.

In the medical manipulator 200, since the gripper holder 230 (rotor) is hollow, an operating means 221 (see FIGS. 10 and 11A) for operating the end effector 212 can be placed substantially centrally in the distal-end working unit 214, making it possible to provide a structure for rolling the distal-end working unit 214 in an unlimited angular range. According to the present embodiment, the movable body 294, the tube 338, the connector 342, the hollow tube 282, and the conductive cable 260 perform a mechanical or electrical action on the end effector 212. According to the present embodiment, these components jointly make up the operating means 221 for operating the end effector 212.

According to the present embodiment, the rotational support tube 232 is disposed outside, not inside, of the gripper holder 230, the space in the gripper holder 230 can be used as a space in which the operating means 221 is disposed, and the distal-end working unit 214 can be simplified in structure. According to the present invention, therefore, the medical manipulator 200 has the distal-end working unit 214 that has a large number of degrees of freedom without constitutive complexities.

In the medical manipulator 200, the engaging members 335 are inserted in the side holes 354 formed in the rotational support tube 232 and also inserted in the annular groove 320 in the gripper holder 230 (rotor) within the rotational support tube 232. Accordingly, the engaging members 335 engage in the annular groove 320 in the axial directions. This engaging structure allows the gripper holder 230 to rotate relatively to the rotational support tube 232 while preventing the gripper holder 230 from axially moving with respect to the rotational support tube 232.

A structure to be described below, though not according to the above embodiment, is also effective to place the gripper holder 230 rotatably, but axially immovably, within the rotational support tube 232. The rotational support tube 232 comprises two separate semicircular members (hereinafter referred to as "segment members"), and the gripper holder 230 has a circumferentially extending annular ridge on an outer circumferential surface thereof whereas each of the segment members of the rotational support tube 232 has a circumferentially extending arcuate groove defined in an inner circumferential surface thereof. To assemble the structure, the gripper holder 230 is surrounded by the two segment members, with the annular ridge placed in the arcuate grooves, and the segment members are then welded to each other. The gripper holder 230 is thus rotatably supported by the inner circumferential surface of the rotational support tube 232. The annular ridge that engages in the arcuate grooves prevents the gripper holder 230 from moving axially with respect to the rotational support tube 232.

The rotational support tube 232 in the form of two segment members poses the following problems: The process of forming the arcuate grooves in the inner circumferential surfaces of the segment members tends to involve an increased number of man-hours to achieve a desired machining accuracy. According to a fabrication process, the rotational support tube 232 that has been manufactured as a unitary product is cut into two segment members, and then annular grooves are formed in the respective inner circumferential surfaces of the two segment members, after which the two segment members are welded to each other. If such a fabrication process is employed, then the arcuate shape of the segment members is liable to spread under internal stresses produced when the arcuate grooves were formed, with the result that the segment members tend to find it difficult to keep a desired tubular shape accuracy when combined together. Even if the rotational support tube 232 is manufactured as a unitary product having a desired tubular shape accuracy by a cutting process, the tubular shape accuracy may possibly be lowered because the rotational support tube 232 is thermally deformed when the segment members are welded to each other. The process of welding the segment members requires an increased number of man-hours due to a large length along which the segment members need to be welded. The above fabrication process has many validation elements.

With the medical manipulator 200 according to the present embodiment, however, the rotational support tube 232 is a unitary product, not a component made up of two segment members welded together, and the engaging members 335 are inserted in the side holes 354 formed in the rotational support tube 232 and engage in the annular groove 320 in the gripper holder 230 within the rotational support tube 232. This engaging structure, which is free of the process of forming grooves, makes it easier to perform accuracy management and requires a smaller number of manufacturing man-hours than the structure wherein the rotational support tube 232 comprises two segment members with arcuate grooves defined in the inner circumferential surfaces thereof, and the gripper holder 230 has an annular ridge on an outer circumferential surface thereof, the annular ridge engaging in the arcuate grooves to prevent the gripper holder 230 from moving axially with respect to the rotational support tube 232. The rotational support tube 232 has its tubular shape accuracy maintained appropriately as it is free from deformations under internal stresses which would otherwise tend to occur if grooves are formed. It is therefore possible to constitute, accurately and simply, a structure wherein a rotor is disposed inside and a rotational support is disposed outside of the rotor.

According to the present embodiment, furthermore, as there is no welding process required to produce the rotational support tube 232 as a tubular product, its tubular shape accuracy is not lowered due to thermal deformations which would otherwise be caused if welded, and the number of man-hours required to produce the rotational support tube 232 is smaller than if two segment members are welded together. The structure according to the present embodiment has fewer validation elements.

According to the present embodiment, in particular, since the engaging members 335 are in the form of a pin each, the area of contact between the engaging members 335 and the annular groove 320 is small to lower frictional resistance therebetween, thereby minimizing resistance to the rotation of the gripper holder 230 with respect to the rotational support tube 232. Consequently, the gripper holder 230 can rotate smoothly with respect to the rotational support tube 232 while at the same time the gripper holder 230 is prevented from moving axially with respect to the rotational support tube 232.

According to the present embodiment, furthermore, since the engaging members 335 are provided at a plurality of locations that are angularly spaced circumferentially around the rotational support tube 232, the engaging members 335 are highly effective to prevent the gripper holder 230 from moving axially with respect to the rotational support tube 232.

According to the present embodiment, the conductive cable 260 disposed in the space 282a in the hollow tube 282 easily provides an electric conduction path leading to the end effector 212 that can be used as a bipolar electrosurgical scalpel, for stably supplying an electric current to the end effector 212. When the gripper holder 230 and the end effector 212 rotate together, the conductive cable 260 housed in the hollow tube 282 also rotate in unison therewith. Consequently, the end effector 212 and the conductive cable 260 (electric conduction path) are reliably prevented from being electrically disconnected from each other.

The medical manipulator 200 according to the present embodiment is electrically rolled by the motor 246, and manually tilted by the user. However, the medical manipulator 200 may be modified such that it is electrically tilted by the motor 246 and manually rolled by the user. According to still another modification of the medical manipulator 200, one or two or more rolling, tilting, and opening and closing movements may be electrically controlled, or the medical manipulator 200 may be rolled, tilted, and opened and closed all manually.

Although the preferred embodiments of the present invention have been described above, it should be understood that the present invention is not limited to the above embodiments, but various changes and modifications made be made to the embodiments without departing from the appended claims.

What is claimed is:

1. A medical manipulator comprising:
a handle;
a shaft extending from the handle;
a distal-end working unit having an end effector, the distal-end working unit being operatively coupled to the shaft for being tilted with respect to the shaft and rolled; and
a force transmitter disposed between the handle and the distal-end working unit, the force transmitter having a portion extending into the distal-end working unit for acting on the end effector;
wherein the distal-end working unit has a rotor rotatable about a roll axis in unison with the end effector, the rotor having a hollow tube, and a rotational support tube having a posture variable with respect to an axial direction of the shaft, wherein the support tube is connected with the shaft through a rigid tilt axis, the rotor being rotatably supported by an inner circumferential surface of the rotational support tube;
the rotor has a circumferentially extending annular groove defined in an outer circumferential surface thereof;
the rotational support tube has at least one side hole extending through a wall thereof between inside and outside surfaces thereof, with an engaging member disposed in the side hole; and
the engaging member is fixed to the rotational support tube while an inner end of the engaging member is inserted in the circumferentially extending annular groove.

2. The medical manipulator according to claim 1, wherein the engaging member is in the form of a pin.

3. The medical manipulator according to claim 2, wherein the engaging member comprises a plurality of engaging members provided at a plurality of locations that are angularly spaced circumferentially around the rotational support tube.

4. The medical manipulator according to claim 2, wherein the engaging member and the rotational support tube are welded to each other by a single joint.

5. The medical manipulator according to claim 2, wherein the engaging member is in form of a screw having an outer thread screwed into a corresponding thread in the side hole.

6. The medical manipulator according to claim 1, wherein the engaging member is in form of a screw having an outer thread screwed into a corresponding thread in the side hole.

7. A medical manipulator comprising:
a handle;
a shaft extending from the handle;
a distal-end working unit having an end effector, the distal-end working unit being operatively coupled to the shaft for being tilted with respect to the shaft and rolled; and
a force transmitter disposed between the handle and the distal-end working unit, the force transmitter having a portion extending into the distal-end working unit for acting on the end effector;
wherein the distal-end working unit has a rotor rotatable about a roll axis in unison with the end effector, the rotor having a hollow tube, and a rotational support tube having a posture variable with respect to an axial direction of the shaft, the rotor being rotatably supported by an inner circumferential surface of the rotational support tube;
the rotor has a circumferentially extending annular groove defined in an outer circumferential surface thereof;
the rotational support tube has at least one side hole extending through a wall thereof between inside and outside surfaces thereof, with an engaging member disposed in the side hole;
the engaging member is fixed to the rotational support tube while an inner end of the engaging member is inserted in the circumferentially extending annular groove; and the engaging member comprises a plurality of engaging members provided at a plurality of locations that are angularly spaced circumferentially around the rotational support tube.

8. The medical manipulator according to claim 7, wherein the engaging member and the rotational support tube are welded to each other by a single joint.

9. The medical manipulator according to claim 7, wherein the engaging member is in form of a screw having an outer thread screwed into a corresponding thread in the side hole.

10. A medical manipulator comprising:
a handle;
a shaft extending from the handle;
a distal-end working unit having an end effector, the distal-end working unit being operatively coupled to the shaft for being tilted with respect to the shaft and rolled; and
a force transmitter disposed between the handle and the distal-end working unit, the force transmitter having a portion extending into the distal-end working unit for acting on the end effector;
wherein the distal-end working unit has a rotor rotatable about a roll axis in unison with the end effector, the rotor having a hollow tube, and a rotational support tube having a posture variable with respect to an axial direction of the shaft, the rotor being rotatably supported by an inner circumferential surface of the rotational support tube;
the rotor has a circumferentially extending annular groove defined in an outer circumferential surface thereof;
the rotational support tube has at least one side hole extending through a wall thereof between inside and outside surfaces thereof, with an engaging member disposed in the side hole;
the engaging member is fixed to the rotational support tube while an inner end of the engaging member is inserted in the circumferentially extending annular groove; and
the engaging member and the rotational support tube are welded to each other by a single joint.

* * * * *